US012670421B2

(12) United States Patent
Sinha et al.

(10) Patent No.: US 12,670,421 B2
(45) Date of Patent: Jun. 30, 2026

(54) INDIVIDUAL TREATMENT ASSIGNMENT FROM MIXTURE OF INTERVENTIONS

(71) Applicant: ADOBE INC., San Jose, CA (US)

(72) Inventors: Gaurav Sinha, Bangalore (IN);
Abhinav Kumar, Amdiha (IN)

(73) Assignee: ADOBE INC., San Jose, CA (US)

( * ) Notice: Subject to any disclaimer, the term of this patent is extended or adjusted under 35 U.S.C. 154(b) by 1174 days.

(21) Appl. No.: 17/671,082

(22) Filed: Feb. 14, 2022

(65) Prior Publication Data

US 2023/0259963 A1      Aug. 17, 2023

(51) Int. Cl.
| | |
|---|---|
| *G06N 7/01* | (2023.01) |
| *G06F 16/23* | (2019.01) |
| *G06Q 30/0242* | (2023.01) |
| *G16H 50/70* | (2018.01) |

(52) U.S. Cl.
CPC ........... *G06N 7/01* (2023.01); *G06F 16/2365* (2019.01); *G06Q 30/0242* (2013.01); *G16H 50/70* (2018.01)

(58) Field of Classification Search
CPC ... G06N 7/01; G06F 16/9024; G06F 16/2365; G06F 16/2264; G06F 16/2321; G06F 16/26; G06F 17/16; G06F 17/18; G06Q 30/0242; G06Q 10/063; G06H 50/70
See application file for complete search history.

(56) References Cited

U.S. PATENT DOCUMENTS

| | | | | |
|---|---|---|---|---|
| 10,614,393 | B2 * | 4/2020 | Jagota | G06F 16/9024 |
| 2016/0292248 | A1 * | 10/2016 | Garcia | G06Q 10/063 |

| | | | | |
|---|---|---|---|---|
| 2018/0025291 | A1 * | 1/2018 | Dey | G06N 7/01 |
| | | | | 706/11 |
| 2022/0004910 | A1 * | 1/2022 | Wei | G06N 20/10 |
| 2022/0093271 | A1 * | 3/2022 | Huang | G16H 50/20 |
| 2022/0198265 | A1 * | 6/2022 | Cintas | G16H 50/70 |
| 2022/0414483 | A1 * | 12/2022 | Shen | G06N 20/10 |

(Continued)

OTHER PUBLICATIONS

Raghu, Vineet K., et al. "Comparison of strategies for scalable causal discovery of latent variable models from mixed data." International journal of data science and analytics 6.1 (2018): 33-45. (Year: 2018).*

(Continued)

*Primary Examiner* — Andrew L Tank
(74) *Attorney, Agent, or Firm* — Shook Hardy & Bacon L.L.P.

(57)          ABSTRACT

An analytics system identifies interventions for individual samples from a set of samples with a mixture of interventions. Given a causal graph, a set of baseline samples, and a set of samples with interventions, a set of intervention tuples is determined that represents the mixture of interventions for the set of samples with interventions. Each intervention tuple in the set of intervention tuples identifies an intervention and a mixing coefficient representing a percentage of samples with the intervention. An iterative process is used in which a set of intervention tuples is determined for N variables and then lifted to a set of intervention tuples for N+1 variables until all variables from the causal graph have been considered, providing a final set of intervention tuples. The final set of intervention tuples is used to match individual samples from the set of samples with interventions to interventions.

17 Claims, 14 Drawing Sheets

(56)         References Cited

U.S. PATENT DOCUMENTS

| | | | |
|---|---|---|---|
| 2023/0051416 A1* | 2/2023 | Porwal | G06F 18/2321 |
| 2023/0229906 A1* | 7/2023 | Zhang | G06N 3/045 |
| | | | 706/21 |
| 2024/0266013 A1* | 8/2024 | Bhave | G16H 50/50 |
| 2024/0274226 A1* | 8/2024 | Rukhlenko | G16B 5/10 |

OTHER PUBLICATIONS

Jaber, Amin, et al. "Causal discovery from soft interventions with unknown targets: Characterization and learning." Advances in neural information processing systems 33 (2020): 9551-9561. (Year: 2020).*

Mooij, Joris M., Sara Magliacane, and Tom Claassen. "Joint causal inference from multiple contexts." Journal of machine learning research 21.99 (2020): 1-108. (Year: 2020).*

Squires, Chandler, Yuhao Wang, and Caroline Uhler. "Permutation-based causal structure learning with unknown intervention targets." Conference on Uncertainty in Artificial Intelligence. PMLR, 2020. (Year: 2020).*

Kumar, Abhinav, and Gaurav Sinha. "Disentangling mixtures of unknown causal interventions." Uncertainty in Artificial Intelligence. PMLR, 2021. (Year: 2021).*

Sussex, Scott, Caroline Uhler, and Andreas Krause. "Near-optimal multi-perturbation experimental design for causal structure learning." Advances in Neural Information Processing Systems 34 (2021): 777-788. (Year: 2021).*

Zhang, Jiaqi, Chandler Squires, and Caroline Uhler. "Matching a desired causal state via shift interventions." Advances in Neural Information Processing Systems 34 (2021): 19923-19934. (Year: 2021).*

* cited by examiner

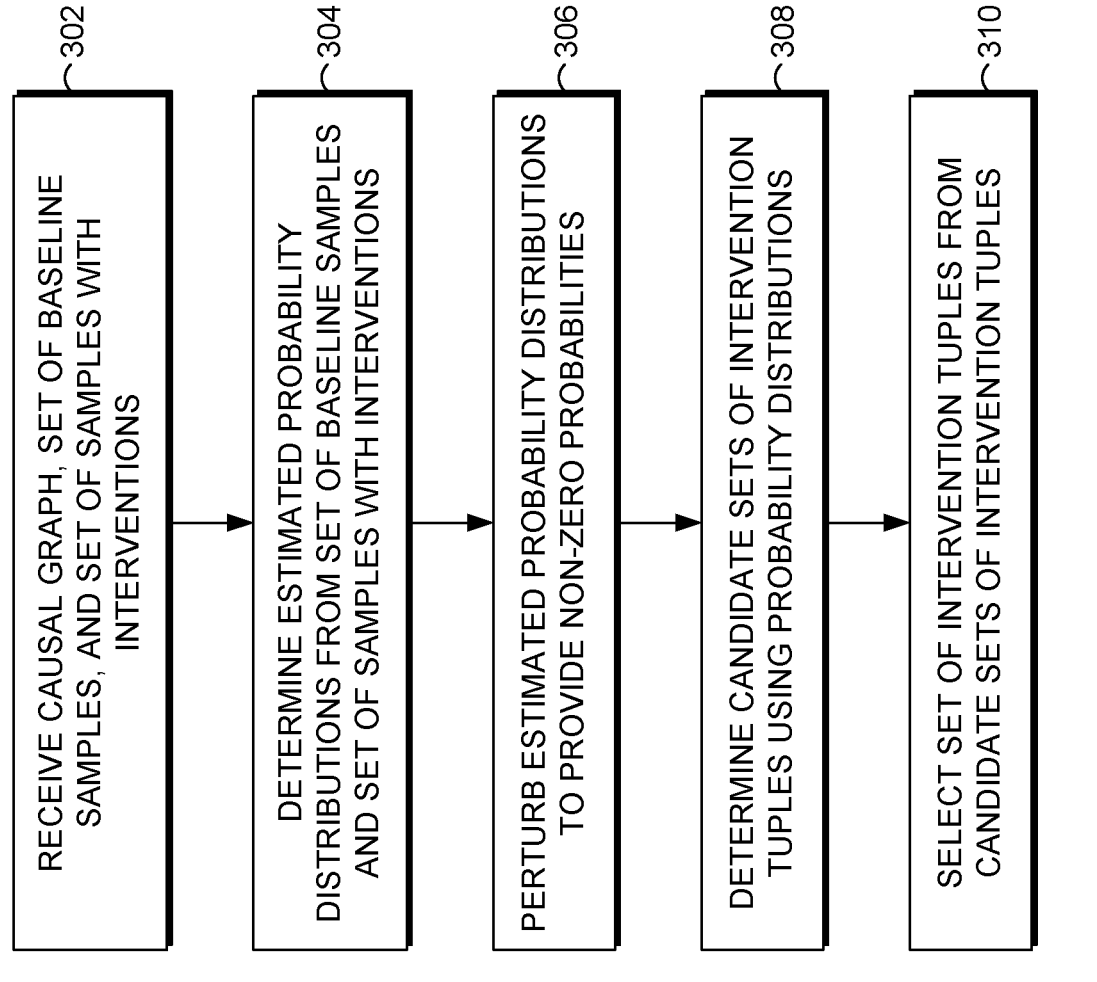

302 — RECEIVE CAUSAL GRAPH, SET OF BASELINE SAMPLES, AND SET OF SAMPLES WITH INTERVENTIONS

304 — DETERMINE ESTIMATED PROBABILITY DISTRIBUTIONS FROM SET OF BASELINE SAMPLES AND SET OF SAMPLES WITH INTERVENTIONS

306 — PERTURB ESTIMATED PROBABILITY DISTRIBUTIONS TO PROVIDE NON-ZERO PROBABILITIES

308 — DETERMINE CANDIDATE SETS OF INTERVENTION TUPLES USING PROBABILITY DISTRIBUTIONS

310 — SELECT SET OF INTERVENTION TUPLES FROM CANDIDATE SETS OF INTERVENTION TUPLES

502 — DETERMINE SET OF INTERVENTION TUPLES

504 — SELECT SAMPLE FROM SET OF SAMPLES WITH INTERVENTIONS

506 — FOR SELECTED SAMPLE, DETERMINE INTERVENTION IN SET OF INTERVENTION TUPLES THAT MAXIMIZES PROBABILITY OF THE SAMPLE GIVEN THE INTERVENTION

508 — MATCH SELECTED SAMPLE TO DETERMINED INTERVENTION

500

['graph_type', 'num_nodes']=('ER', 4)
['graph_type', 'num_nodes']=('ER', 8)
['graph_type', 'num_nodes']=('ER', 12)
['graph_type', 'num_nodes']=('SF', 4)
['graph_type', 'num_nodes']=('SF', 8)
['graph_type', 'num_nodes']=('SF', 12)

['graph_type', 'num_nodes']=('ER', 4)
['graph_type', 'num_nodes']=('ER', 8)
['graph_type', 'num_nodes']=('ER', 12)
['graph_type', 'num_nodes']=('SF', 4)
['graph_type', 'num_nodes']=('SF', 8)
['graph_type', 'num_nodes']=('SF', 12)

INDIVIDUAL TREATMENT ASSIGNMENT FROM MIXTURE OF INTERVENTIONS

BACKGROUND

Understanding the treatment effect of interventions on a desired outcome is one of the main components of prescriptive analysis in the sciences and social sciences. In some instances, known interventions are taken on a system and the effect of the interventions can be analyzed. However, there are many situations where data being analyzed contains samples that result from unintended/unknown interventions. For example, unknown interventions often occur in gene knockout techniques. These gene knockout techniques are intended to target a particular genome. However, experiments have been observed to have off target effects which create unwanted and hidden manipulations in the genome. As another example, an unknown intervention can occur in a system analyzing promotional emails when a promotional email ends up in a spam folder and therefore never reaches a targeted individual. Similarly, an automated campaign might end up sending an email with incorrect or unintended content. In such scenarios, different samples can get randomly exposed to different unknown interventions, thereby creating a mixture of interventions.

SUMMARY

Embodiments of the present invention relate to, among other things, an analytics system that identifies interventions for individual samples from a set of samples with a mixture of interventions. Given a causal graph, a set of baseline samples, and a set of samples with interventions, a set of intervention tuples is determined that represents the mixture of interventions for the set of samples with interventions. Each intervention tuple in the set of intervention tuples identifies an intervention and a mixing coefficient representing a percentage of samples with the intervention. An iterative process is used in which a set of intervention tuples is determined for N variables and then lifted to a set of intervention tuples for N+1 variables until all variables from the causal graph have been considered, providing a final set of intervention tuples.

At each iteration, the set of intervention tuples for N+1 variables is determined by solving a system of equations using probability distributions calculated over the N+1 variables. In some instances, the probability distributions are perturbed to ensure all probabilities are positive. The system of equations are solved by setting each mixing coefficient to zero one at a time to determine values for remaining mixing coefficients. This provides a number of candidate sets of intervention tuples, and the set of intervention tuples for the N+1 variables is selected from the candidate sets (e.g., based on an L2 norm for each candidate set).

Once the set of intervention tuples has been determined for all variables in the causal graph, individual samples from the set of samples with interventions are matched to interventions based on the set of intervention tuples. This can include assigning a sample to an intervention that maximizes the probability that the sample resulted from the intervention.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein:

FIG. 3 is a flow diagram showing a method for determining a set of intervention tuples given a single variable in accordance with some implementations of the present disclosure;

DETAILED DESCRIPTION

Definitions

Figure 1:
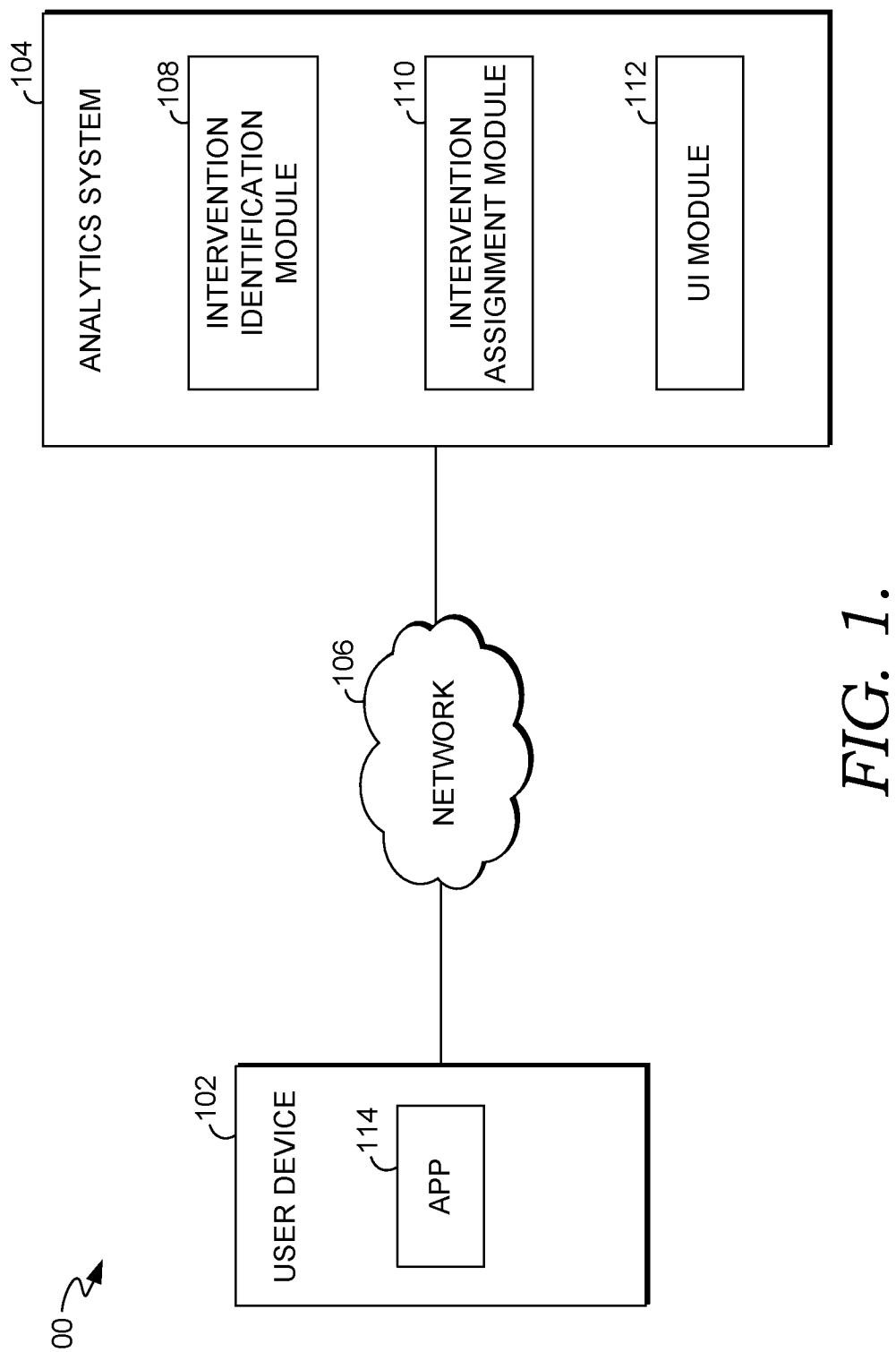
FIG. 1 is a block diagram illustrating an exemplary system in accordance with some implementations of the present disclosure.

Various terms are used throughout this description. Definitions of some terms are included below to provide a clearer understanding of the ideas disclosed herein.

Notation: Capital letters (e.g., X) are used herein to represent random variables and the corresponding lower case letter x to denote the assignment X=x. The set of values taken by random variable X will be denoted by $C_X$. Each random variable can be discrete and have finite support i.e. $|C_X| < \infty$. A tuple or set of random variables is denoted by capital bold face letter (e.g., X) and the corresponding lower case bold faced letter x denotes the assignment X=x. Let, $C_X = \Pi_{X_i \in X} C_{X_i}$ denote the set of all possible values that can be taken by X. Probability of X taking the value x is denoted by $\mathbb{P}(X=x)$ or equivalently as $\mathbb{P}(x)$ and probability of X=x given Y=y is denoted as $\mathbb{P}(X=x|Y=y)$ or equivalently with $\mathbb{P}(x|y)$. Additionally, [n] is used to denote the set $\{1, 2, \ldots, n\}$, [m, n] to denote set $\{m, m+1, \ldots, n\}$, calligraphic capital letters e.g. $\mathcal{S}$ to denote sets. Size of any set $\mathcal{S}$ is denoted by $|\mathcal{S}|$. $\mathbb{R}$, $\mathbb{R}_+$, and $\mathbb{R}_{\geq 0}$ will denote the set of real numbers, positive real numbers and non-negative real numbers respectively.

As used herein, a "causal graph" depicts causal relationships among a set of variables. The causal graph can include a number of nodes with edges between the nodes. Each node corresponds with a variable and each edge represents a causal relationship between two nodes/variables. The variables can include treatment variables, co-variates, and outcomes. In some instances, the causal graph comprises a directed acyclic graph (DAG). The casual graph can be manually generated using expert knowledge or learned from observational data (e.g., feeding observational data into known algorithms for learning a causal graph). Let $\mathcal{G}=\{V, \in\}$ be a DAG with node set $V=\{V_1, \ldots, V_n\}$ where each node $V_i$ represents a random variable. $\mathcal{G}$ is called a Bayesian Network if the following factorization of the joint probability of V holds.

$$\mathbb{P}(v) = \prod_{V_i \in V} \mathbb{P}(v_i \mid pa(v_i))$$

where $pa(V_i)$ are parent nodes of $V_i$. A causal Bayesian Network (CBN) is a Bayesian Network where all edges denote direct causal relationships. It allows for modeling effect of external actions called "interventions", by appropriate modification of the Bayesian Network.

An "intervention" comprises an external action on a system under investigation that sets a particular value for a variable. For example, an intervention can comprise administration of a dosage of medicine to a patient. In some cases, an intervention is known or intended; while in other cases, an intervention is unknown or unintended. For example in the case of gene-editing, a known/intended intervention occurs when a certain target gene is spliced out and replaced with the desired gene. However, the gene-editing also causes unintended cleavage at unknown genome sites, which comprise unknown/unintended interventions.

A natural way to model interventions in causal Bayesian Networks is to perform the act of causal surgery, wherein, incoming edges into the node(s) to be intervened are removed and the node(s) is forcibly fixed to the desired value. The new network thus obtained is treated as the Bayesian Network modelling effect of the intervention. Formally, if intervention is performed on nodes $X \subseteq V$ with a desire to set it to value $x^* \in C_X$, then the effect of this intervention (also known as interventional distribution) is a probability distribution on V denoted as $\mathbb{P}(v \mid do(x^*))$ (or $\mathbb{P}_{x^*}(v)$). In the intervened Bayesian Network, conditional probability distributions (CPD) $\mathbb{P}(X_i \mid pa(X_i))$ of all $X_i \in X$ that are intervened and set to $x_i^*$, changes to the Kronecker delta function $\delta_{x_i, x_i^*}$, i. e. $\mathbb{P}(X_i = x_i \mid pa(X_i))=1$ if $x_i = x_i^*$ else it is 0. The CPD of the non-intervened nodes, i.e., $V \backslash X$, remains unchanged. Hence the interventional distribution factorizes as:

$$\mathbb{P}_{x^*}(v) = \prod_{V_i \notin X} \mathbb{P}(v_i \mid pa(v_i)) \prod_{V_i \in X} \delta_{v_i, x_i^*}$$

A "mixture of interventions" comprises a system in which multiple known and/or unknown interventions have occurred. Let $\mathcal{G}=\{V, \varepsilon\}$ be a causal Bayesian Network. A probability distribution $\mathbb{P}_{mix}(V)$ is called a mixture of interventions if for some $m \in \mathbb{N}$, there exist subsets $T_1, \ldots, T_m \subseteq V$, corresponding values $t_i \in C_{T_i}$ and positive scalar weights $\pi_i \in \mathbb{R}_+$, $i \in [m]$, such that:

$$\mathbb{P}_{mix}(V) = \sum_{i=1}^{m} \pi_i \mathbb{P}_{t_i}(V)$$

4 where $t_i \neq t_j$ for all $i \neq j \in [m]$ (if, $t_i = t_j$ then $(\pi_i + \pi_j) \mathbb{P}_{t_i}(V)$ is one component). Allowing $T_i = \emptyset$, in which case, $\mathbb{P}_{t_i}(V)$ is defined as $\mathbb{P}(V)$. Note that for $\mathbb{P}_{mix}$ to be a valid distribution $$\sum_{i=1}^{m} \pi_i = 1.$$

The set $\mathcal{T}=\{\{t_i, \pi_i\}, i \in [m]\}$ is referred to as a "set of intervention tuples" generating the mixture.

An "intervention tuple" comprises an identification of an intervention $(t_i)$ and a mixing coefficient $(\pi_i)$ associated with the intervention. The intervention can comprise a set value for a given variable. The mixing coefficient specifies a percentage of a population having the corresponding intervention.

A "sample" refers to an individual observation of data from an overall collection of data. A sample can provide an indication of a value for each of a number of variables. For example, a sample can identify a patient, the patient's age, the patient's gender, whether the patient received a vaccine, and an outcome for the patient. As another example, a sample can correspond with an instance of a marketing email for an individual, specifying a number of past marketing emails opened by the individual, a subject line for a current marketing email, and an indication of whether the individual opened the current marketing email.

Overview

Current analytics systems often use causal graphs, such as Causal Bayesian Networks (CBN), to model causal relationships in many real-world systems. These models can simulate the effects of external interventions that forcibly fix target system variables to desired target values. The simulation is done via the do( ) operator, wherein the CBN is altered by breaking incoming edges of the target variables and fixing them to desired target values. These interventions on the CBN can be used to estimate the effects of treatments on desired outcomes. However, real-world interventions are not always precise and might end up as incorrect, unknown and unintended. There are often situations where data being analyzed contains samples of many such unintended/unknown interventions.

As an example to illustrate, consider an email marketing system that sends email promotions with two possible subject line options: Subject_1 or Subject_2. For each customer, the subject line is selected depending on how many emails the customer has opened in the past. Individuals who engaged more in the past get Subject_1 (with high probability) and those who engage less get Subject_2 (with high probability). Finally, at the end of the promotion duration, for each customer, information is obtained on whether the email was opened by the customer or not. The data is used to generate a CBN with three variables: "Past_Opens", "Treatment", and "Open". The Past_Opens variable denotes the co-variate indicating the number of emails opened by the customer in the past. The Treatment variable denotes which of the two subject lines was sent to the customer. The Open variable is the outcome and can be one of {Yes, No}. Customer data from historical campaigns (and experiments if necessary) can be used to estimate the conditional probabilities P(Open|Treatment, Past_Opens), P(Treatment|Past_Opens) and P(Past_Opens) and therefore have a complete description of the CBN.

Now consider a new campaign, where an unknown and unintended intervention occurs at the customer's end. For instance, consider a customer who has made many opens in the past and therefore was sent an email with subject line Subject_1. However, due to a new spam filter deployed by the customer's email provider, the email gets filtered as spam and therefore never gets opened. The analytics systems has no knowledge of the spam filter, and it could be assumed that the email was not opened because the customer was not interested. In general, many such unknown interventions on different customers might be happening, making this problem quite challenging for the analytics system to resolve. Identifying which customer went through which unknown interventions could be of high value.

As another example, gene knockout experiments via the CRISPR-Cas9 gene-editing technology are intended to target known genome sites. However, the technology results in unintended cleavage at unknown genome sites. Moreover, the unintended intervention targets can themselves be noisy; i.e., different individuals targeted by the same intervention might undergo completely different off-target interventions. For example, some studies have demonstrated that the same gene editing experiment (using CRISPR-Cas9) on mice embryos exhibited different unintended cleavage for different mice.

In both the above situations, samples (e.g., individual customers or gene-editing targets) that underwent different unintended (or no) interventions are not segregated and therefore the generated distribution becomes a mixture of individual interventional distributions.

Some existing solutions have been proposed for this problem but the solutions have drawbacks. For instance, one solution employs an algorithm to learn such unintended interventions under the assumption that each unintended intervention is only on a single variable. This is a very restrictive assumption since the unintended intervention is generally not in control and could be possibly affecting multiple treatment variables. This can be seen by extending the above marketing example to have two treatment variables, the promotional email (i.e., email promotions with two possible subject line options: Subject_1 or Subject_2) and an app notification. It's possible that some customers who were affected by the unintended intervention due to the spam filter also disable notifications on their phone leading to an unintended and unknown intervention on two variables. The existing solution does not tackle this situation and only works when all unintended interventions are on a single variable.

Another existing technique uses a brute force algorithm to solve this problem. However, in the case of N variables with k categories each, there are $\Omega(k^N)$ such possible interventions and therefore the system is over exponentially many variables. This makes it infeasible for even very small values of N.

Embodiments of the present invention solve these problems by providing an analytics system that identifies interventions for individual samples from a set of samples having a mixture of interventions. The mixture of interventions includes known and/or unknown interventions. As will be described in further detail herein, some configurations of the technology described herein enforces two conditions to determine interventions and their mixing coefficients (percentage of samples) in the mixture of interventions. The first condition is that a given system satisfies positivity; i.e., the probability distributions generated from samples have all positive probabilities. The second condition is that a set of intervention tuples (interventions and their corresponding mixing coefficients) satisfy exclusion; i.e. some setting of each variable is missing from the mixture. Using these two conditions, a set of intervention tuples can be determined for samples with a mixture of interventions, and the set of intervention tuples can in turn be used to match individual samples to interventions.

In accordance with some aspects of the technology described herein, a set of samples having a mixture of interventions is received for which assignment of individual samples to interventions is to be determined. Additionally, a causal graph and a set of baseline samples (i.e., samples without the unknown mixture of interventions) are received. Given the causal graph, set of baseline samples, and set of samples with interventions, a set of intervention tuples is determined, representing the mixture of interventions. Each intervention tuple in the set of intervention tuples identifies an intervention (i.e., setting of a particular variable to a particular value) and a mixing coefficient for the intervention (i.e., a percentage of the samples, from the set of samples having interventions, for which that intervention contributed to the samples).

The set of intervention tuples is determined using an iterative process in which a set of intervention tuples is determined for N variables and then lifted to a set of intervention tuples for N+1 variables. For instance, given a causal graph with three variables, a set of intervention tuples is initially be determined for a first variable from the causal graph and that set of intervention tuples lifted to a set of intervention tuples for the first variable and a second variable, which is then lifted to a set of intervention tuples for all three variables. The order in which the variables are selected can be based on a topological ordering of the variables in the causal graph.

To determine the set of intervention tuples at each iteration, a system of equations is generated and solved using probability distributions estimated on the number of variables under consideration for the iteration. The probability distributions are estimated given the set of baseline samples and the set of samples with interventions. In some configurations, positivity is enforced by perturbing the probability distributions such that all probabilities are greater than zero. To solve the system of equations, exclusion is enforced by setting each mixing coefficient to zero one at a time to provide candidate sets of interventions tuples (i.e., a candidate set of intervention tuples for each time a mixing coefficient is set to zero). A set of intervention tuples is selected from the candidate sets of intervention tuples. For instance, an L2 norm can be computed for each candidate set of intervention tuples, and the set of intervention tuples having the lowest L2 norm is selected. In some configurations, a threshold is employed such that any mixing coefficient less than the threshold is set to zero and remaining mixing coefficients renormalized. This ensures that any intervention with a low mixing coefficient is removed from consideration.

Once the set of intervention tuples has been determined for all variables in the causal graph, individual samples from the set of samples with interventions are matched to interventions based on the set of intervention tuples. This can include determining, from the set of intervention tuples, the intervention that maximizes the probability that the sample resulted from the intervention. The sample can then be assigned to that intervention.

The technology described herein provides a number of advantages over conventional approaches. For instance, the technology described herein can identify a mixture of interventions and assign interventions to samples for systems having any number of variables. This is in contrast to some solutions that are limited to determining inventions for a single variable. While brute force approaches are not limited to a single variable, in the case of N variables with k categories each, there are $\Omega(k^N)$ such possible interventions and the system is over exponentially many variables, thereby making it infeasible for even very small values of N. In contrast, time complexity of the technology described herein does not have an exponential dependence on N, thereby making it more efficient. As will be described in further detail below, the approach of the technology described herein is compared to the brute force approach for a small graph (due to the reason just mentioned), demonstrating better performance of the technology described herein even with smaller graphs. For causal graphs with even moderate number of nodes, the brute force becomes intractable, while the approach of the technology described herein can operate on such graphs.

Example System for Identifying Interventions

With reference now to the drawings, FIG. 1 is a block diagram illustrating an exemplary system 100 for identifying interventions in a set of samples with a mixture of interventions and matching interventions to individual samples in accordance with implementations of the present disclosure. It should be understood that this and other arrangements described herein are set forth only as examples. Other arrangements and elements (e.g., machines, interfaces, functions, orders, and groupings of functions, etc.) can be used in addition to or instead of those shown, and some elements can be omitted altogether. Further, many of the elements described herein are functional entities that can be implemented as discrete or distributed components or in conjunction with other components, and in any suitable combination and location. Various functions described herein as being performed by one or more entities can be carried out by hardware, firmware, and/or software. For instance, various functions can be carried out by a processor executing instructions stored in memory.

The system 100 is an example of a suitable architecture for implementing certain aspects of the present disclosure. Among other components not shown, the system 100 includes a user device 102 and an analytics system 104. Each of the user device 102 and analytics system 104 shown in FIG. 1 can comprise one or more computer devices, such as the computing device 900 of FIG. 9, discussed below. As shown in FIG. 1, the user device 102 and the analytics system 104 can communicate via a network 106, which can include, without limitation, one or more local area networks (LANs) and/or wide area networks (WANs). Such networking environments are commonplace in offices, enterprise-wide computer networks, intranets, and the Internet. It should be understood that any number of user devices and servers can be employed within the system 100 within the scope of the present invention. Each can comprise a single device or multiple devices cooperating in a distributed environment. For instance, the analytics system 104 could be provided by multiple server devices collectively providing the functionality of the analytics system 104 as described herein. Additionally, other components not shown can also be included within the network environment.

At a high level, given a set of samples with a mixture of interventions, the analytics system 104 identifies interventions and matches the interventions to individual samples. As shown in FIG. 1, the analytics system 104 includes an intervention identification module 108, an intervention assignment module 110, and a user interface (UI) module 112. These components can be in addition to other components that provide further additional functions beyond the features described herein.

The analytics system 104 can be implemented using one or more server devices, one or more platforms with corresponding application programming interfaces, cloud infrastructure, and the like. While the analytics system 104 is shown separate from the user device 102 in the configuration of FIG. 1, it should be understood that in other configurations, some or all of the functions of the treatment effect system 104 can be provided on the user device 102.

The analytics system 104 operates on inputs that include a causal graph, a set of baseline samples, and a set of samples with interventions. The causal graph provides information regarding causal relationships among variables for a system being analyzed. Prior knowledge of the system along with state of the art algorithms can be used to learn the causal graph when no unknown interventions happen. The set of baseline samples comprises a collection of samples in which unknown interventions have not occurred. The set of samples with a mixture of interventions comprises samples in which an unknown intervention has occurred in at least some of the samples.

Figure 2:
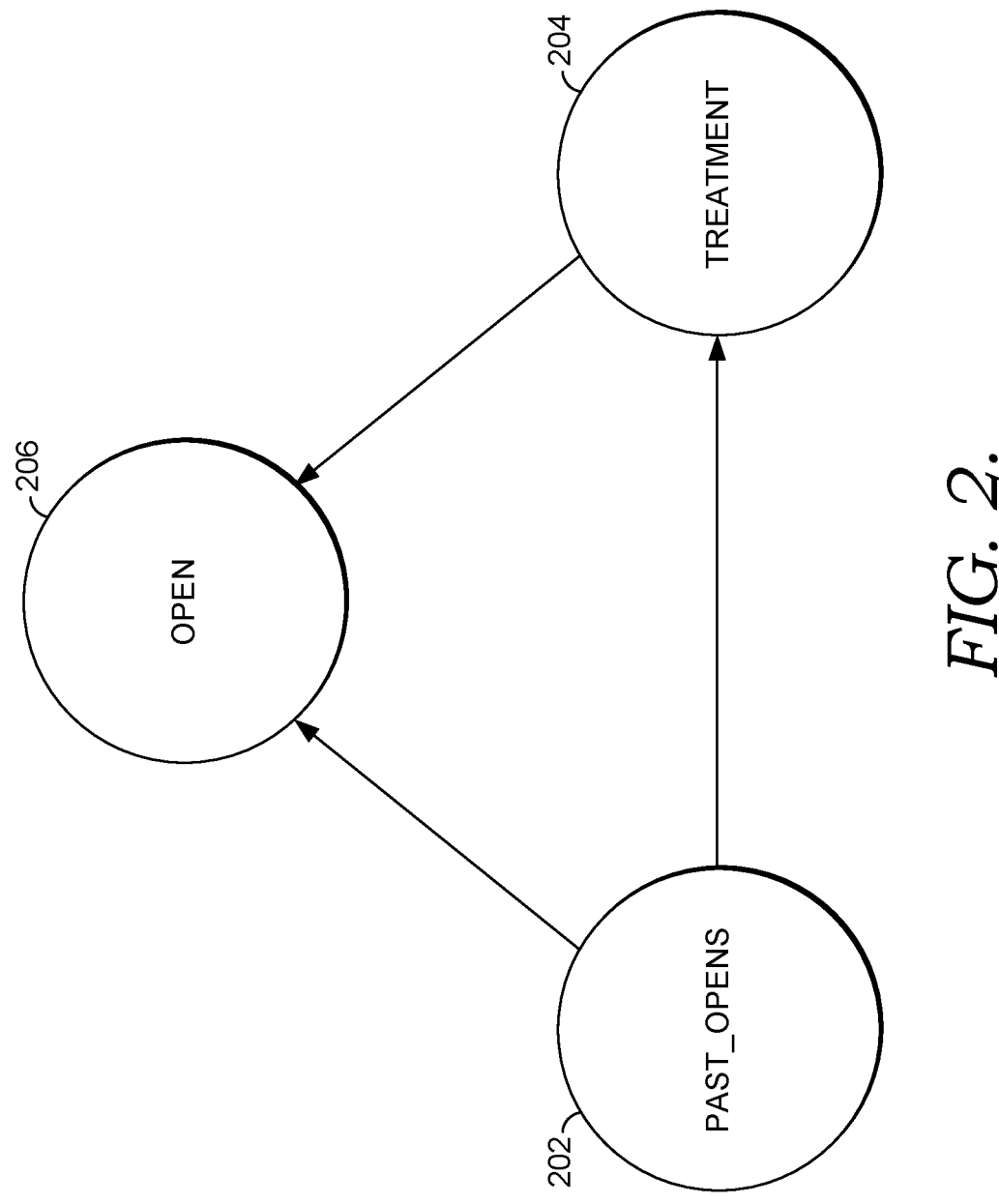
FIG. 2 is a diagram showing an example of a causal graph that can be used in accordance with some implementations of the present disclosure.

By way of example for illustration purposes, FIG. 2 illustrates a causal graph 200 for an email marketing scenario in which an email marketing system sends email promotions with two possible subject line options: Subject_1 or Subject_2. For each customer, the subject line is selected depending on how many emails the customer has opened in the past. Individuals who engaged more in the past get Subject_1 (with high probability) and those who engage less get Subject_2 (with high probability). Finally, at the end of the promotion duration, for each customer, information is obtained on whether the email was opened by the customer or not. The data is used to generate the causal graph 202 with three variables: "Past_Opens" 202, "Treatment" 204, and "Open" 206. The Past_Opens variable 202 denotes the co-variate indicating the number of emails opened by the customer in the past. The Treatment variable 204 denotes which of the two subject lines was sent to the customer. The Open variable 206 is the outcome and can be one of {Yes, No}. A set of baseline samples can be accessed from customer data from historical campaigns (and experiments if necessary) and used to estimate the conditional probabilities P(Open|Treatment, Past_Opens), P(Treatment|Past_Opens) and P(Past_Opens). A set of samples with interventions can be provided when a new campaign with a mix of interventions occurs (including unknown and unintended interventions). An unknown intervention could occur on any of the variables in the causal graph 200. For instance, due to a new spam filter deployed by one individuals email provider, the email gets filtered as spam and therefore never gets opened. As another example, although the number of past opens by an individual indicates the individual should receive an email with Subject_1, the system inadvertently sends an email with Subject_2. As can be understood, a system with a larger number of variables and values for each variable could experience a large number of interventions.

Let $\mathcal{G} = \{V, \varepsilon\}$ be a causal graph (e.g., a causal Bayesian Network) and $\mathbb{P}(V)$ be the associated joint probability distribution. Let $\mathbb{P}_{mix}(V)$ be any mixture of interventions with the set of intervention tuples $\mathcal{T} = \{(t_1, \pi_1), \ldots, (t_m, \pi_m)\}$. The analytics system 104 is given access to $\mathcal{G}$ and finitely many samples from $\mathbb{P}(V)$ (i.e., set of baseline samples) and $\mathbb{P}_{mix}(V)$ (i.e., set of samples with a mixture of interventions). The intervention identification module 108 determines the set of unknown interventions in $\mathcal{T}$. The intervention assignment module 110 determines, for each given sample from $\mathbb{P}_{mix}(V)$, the actual intervention (from the ones in $\mathcal{T}$) that the sample got generated as a result of.

In accordance with aspects of the technology descried herein, each of the interventions $t_i$, corresponds to an intervention that intentionally or unintentionally transpired. Since the ultimate goal of the intervention identification module 108 is to recover the interventions $t_i$ from the mixture distribution, the intervention identification module 108 "uniquely" defines the mixture. Formally, there should not exist two distinct sets of intervention tuples $$\mathcal{T}_1 = \{(t_1^1, \pi_1^1), \ldots, (t_n^1, \pi_n^1)\} \text{ and } \mathcal{T}_2 = \{(t_1^2, \pi_1^2), \ldots, (t_m^2, \pi_m^2)\}$$

which generate the same mixture distribution, i.e., $$\mathbb{P}_{mix}(V) = \sum_{i=1}^{n} \pi_i^1 \mathbb{P}_{t_i^1}(V) = \sum_{j=1}^{m} \pi_j^2 \mathbb{P}_{t_j^2}(V)$$

Given access to a causal graph and the joint distribution $\mathbb{P}(V)$ it captures, the intervention identification module 108 takes as input the mixture distribution $\mathbb{P}_{mix}(V)$ and recovers the unknown set of intervention tuples that generated $\mathbb{P}_{mix}(V)$ by employing two mild assumptions to provide uniqueness and identifiability.

The first assumption is referred to herein as "positivity." Let V be the set of nodes in the causal graph and $\mathbb{P}(V)$ be the corresponding joint probability distribution. Positivity assumes that $\mathbb{P}(v)>0$ for all $v \in C_V$. The second assumption is referred to herein as "exclusion." Let $\mathcal{T}$ be a set of intervention tuples. $\mathcal{T}$ satisfies exclusion, if for all $V_i \in V$, there exists $\bar{v}_i \in C_{V_i}$ such that $\bar{v}_i \notin t$ for any target t belonging to any tuple in $\mathcal{T}$. A mixture of interventions $\mathbb{P}_{mix}(V)$ satisfies exclusion if some set of intervention tuples $\mathcal{T}$ generating it satisfies exclusion. The incorporation of these two assumptions into the process of identifying unknown interventions from a mixture of interventions will be described in further detail below.

Given the set of baseline samples and the set of samples with interventions, the intervention identification module 108 estimates marginal and conditional probabilities of the underlying distributions. For instance, the set of baseline samples can be represented by $\mathcal{B}=\{b_1, \ldots, b_M\}$ where $b_i \sim \mathbb{P}(V)$, and the set of samples with interventions can be represented by $$\mathcal{B}_{mix} = \{b_1^{mix}, \ldots, b_M^{mix}\} \text{ where } b_j^{mix} \sim \mathbb{P}_{mix}(V).$$

The intervention identification module 108 enforces positivity on the estimates by ensuring that all probabilities are non-zero. This can be done by perturbing the distributions slightly, for instance, using a small positive constant 6 such that all probabilities are non-zero.

The intervention identification module 108 uses the probability distribution estimates to determine the set of intervention tuples. Each intervention tuple in the set identifies a particular intervention (i.e., setting a variable to a certain value) and a corresponding mixing coefficient (i.e., a percentage of a population that received the intervention). The following description first discusses the determination of a set of intervention tuples given a single variable. This is followed by a description of determining a set of intervention tuples for a system with multiple variables by iteratively lifting a solution from N variables to N+1 variables.

Single Variable: When there is a single variable (i.e., $|V|=1$, say $V=\{V\}$), the most general form of $\mathbb{P}_{mix}$ (i.e. allowing for scalar weights to be $\geq 0$) can be written as:

$$\mathbb{P}_{mix}(V) = \pi_0 \mathbb{P}_{t_0}(V) + \pi_1 \mathbb{P}_{t_1}(V) + \ldots + \pi_k \mathbb{P}_{t_k}(V) \qquad (1)$$

where $t_0=\emptyset$, $t_1=v^1$, . . . , $t_k=v^k$ are intervention targets corresponding to the different possible values $v^1, \ldots, v^k$ of V with $\pi_0=1-(\pi_1+ \ldots +\pi_k)$.

Since the intervention identification module 108 only has access to estimates $\mathbb{N}$, $\mathbb{N}_{mix}$ of $\mathbb{P}$, $\mathbb{P}_{mix}$ respectively, the intervention identification module 108 sets up the above system using these estimates. In particular, equation (1) is rearranged to get a system of the form $A\pi=b$ given as, $$\begin{bmatrix} 1-a_1 & -a_1 & \cdots & -a_1 \\ -a_2 & 1-a_2 & \cdots & -a_2 \\ \cdot & & \cdots & \cdot \\ -a_k & -a_k & \cdots & 1-a_k \end{bmatrix} \begin{bmatrix} \pi_1 \\ \pi_2 \\ \cdot \\ \pi_k \end{bmatrix} = \begin{bmatrix} b_1 \\ b_2 \\ \cdot \\ b_k \end{bmatrix} \qquad (2)$$

where $b_i= \mathbb{N}_{mix}(v^i)- \mathbb{N}(v^i)$ and $a_i= \mathbb{N}(v^i)>0$ (i.e., enforcing positivity).

To enforce exclusion, the intervention identification module 108 sets each mixing coefficient to zero one at a time and solves the system of equations (2) using the probability estimates ($\mathbb{N}$, $\mathbb{N}_{mix}$) to determine the values for the mixing coefficients ($\pi_1, \ldots, \pi_k$). This provides a number of candidate sets of intervention tuples. In particular, for every mixing coefficient that is set to zero, a candidate set of intervention tuples ($\mathcal{T}=\{t_i, \pi_i\}:i \in [k]$) is determined. For instance, $\pi_1$ is set to zero and the system of equations (2) is solved to determine mixing coefficients for a first candidate set of intervention tuples; $\pi_2$ is set to zero and the system of equations (2) is solved to determine mixing coefficients for a second candidate set of intervention tuples; etc. For every such candidate set of intervention tuples $\mathcal{T}$, the intervention identification module 108 iterates through the tuples ($t_i, \pi_i$) and set any non-zero mixing coefficient to zero (i.e., if some $\pi_i<0$, set $\pi_i \leftarrow 0$.

The intervention identification module 108 compares the candidate sets of intervention tuples to select one as the set of intervention tuples. In some configurations, the intervention identification module 108 computes the L2 norm for each candidate set of intervention tuples, and select the candidate set of intervention tuples with the lowest L2 norm. For instance, this can comprise computing the score $r(\mathcal{T})=\|A\pi-b\|^2$ and selecting a set of intervention tuples $\mathcal{T}$ with the smallest value of $r(\mathcal{T})$.

In some configurations, a threshold $\epsilon$ can be employed such that only mixing coefficients greater than the threshold are retained. Any mixing coefficient below the threshold is set to zero, and the remaining mixing coefficients above the threshold can be renormalized.

Selection of the threshold E impacts the time complexity of the system as follows:

$$\left( \frac{N k_{max}^d M}{\epsilon} \right)^{O(1)} \qquad (3)$$

N is number of nodes in the causal graph G, d is the maximum in-degree of any node, $k_{max}$ is maximum number of values that any node in G can take and M is the number of samples present in $\mathcal{B}$ and $\mathcal{B}_{mix}$. Since the algorithm's run-time depends on $\in$, the value of $\in$ can be selected based on desired outcomes. Setting E too small could increase the run time, whereas setting E too big could lead to pruning interventions with significant mixing proportions present in the mixture.

Multiple Variables:

Where the system includes multiple variables, the intervention identification module 108 reduces to a problem with N variables and, using a recursive call to this function, computes its solution. The computed solution for N variables is lifted to a solution on N+1 variables. By way of example to illustrate with reference to the causal graph 200 of FIG. 2, the intervention identification module 108 initially reduces the problem to a single variable—i.e., the Past_Opens variable 202—and determines a set of intervention tuples given the single variable. The intervention identification module 108 then lifts that solution to two variables—i.e., the Past_Opens variable 202 and the Treatment variable 204—to provide a set of intervention tuples given the two variables. The intervention identification module 108 then lifts that solution to three variables—i.e., the Past_Opens variable 202, the Treatment variable 204, and the Open variable 206—to provide a set of intervention tuples given the three variables. The following discussion discusses this process.

At each iteration, the intervention identification module 108 reduces from N+1 variables to N variables. Let $V_1 \prec \ldots \prec V_{N+1}$ denote a topological order in G. The approach marginalizes on $V_{N+1}$ to create access to $\widehat{\mathbb{P}}_{mix}(V_N)$ and $\widehat{\mathbb{P}}(V_N)$ where $V_N=(V_1, \ldots, V_N)$ and constructs $G_N=G\backslash\{V_{N+1}\}$. This algorithm is recursively called with inputs $G_N$, $\widehat{\mathbb{P}}(V_N)$, $\widehat{\mathbb{P}}_{mix}(V_N)$ to obtain the set of intervention tuples $\mathcal{S}=\{(s_1, \mu_1), \ldots, (s_q, \mu_q)\}$.

The invention identification module lifts the solution for N variables to N+1 variables. To lift the set of intervention tuples $\mathcal{S}$ for N variables to a set of intervention tuples $\mathcal{T}$ for N+1 variables, it is first noted that the only intervention components that can appear in the original mixture are of the form $s_i\cup\{v^j\}$, $i\in\{1, \ldots, q\}$, $j\in\{1, \ldots, k\}$. Here $v^1, \ldots, v^k$ are all possible values of the variable $V_{N+1}$. Therefore the original mixture has the form:

$$\mathbb{P}_{mix}(V_1, \ldots, V_{N+1}) = \sum_{i=1}^{q}\sum_{j=1}^{k}\pi_{s_i\cup\{v^j\}}\mathbb{P}_{s_i\cup\{v^j\}}(V_1, \ldots, V_{N+1}) \quad (4)$$

where $\pi_{s_i\cup\{v^j\}}\geq 0$ are non negative scalars that sum up to 1. This equation can be evaluated at different settings which simplifies the system significantly. For this, let $s_1, \ldots, s_q$ be ordered such that $i\leq j$ implies that $s_j\subseteq s_i$. For all $i\in[N]$, by inspecting $s_j$, identify $\hat{v}_i\in C_{V_i}$ such that $\hat{v}_i\notin s_j$ for any $j\in[q]$ (this holds due to exclusion). Define $s_{-j}=\{\hat{v}_i: V_i\notin S_j\}$. Let $C_{V_{N+1}}=\{v^1, \ldots, v^k\}$. For each $i\in[q]$ and $l\in[k]$, create setting $v_{i,l}=s_i\cup s_{-i}\cup\{v^l\}$. Note that the estimated distributions $\widehat{\mathbb{P}}$, $\widehat{\mathbb{P}}_{mix}$ are used in the above equation. For each $i\in[q]$, evaluating the equation at different $v_{i,l}$, $l\in[k]$ gives a system of equations $A\pi=b$ as follows:

$$\begin{bmatrix} c-a_1 & -a_1 & \cdot & \cdot & -a_1 \\ -a_2 & c-a_2 & \cdot & \cdot & -a_2 \\ \cdot & \cdot & \cdot & \cdot & \cdot \\ -a_k & -a_k & \cdot & \cdot & c-a_k \end{bmatrix}\begin{bmatrix} x_1 \\ x_2 \\ \cdot \\ x_k \end{bmatrix} = \begin{bmatrix} b_1 \\ b_2 \\ \cdot \\ b_k \end{bmatrix} \quad (5)$$

In the above system, the known values are renamed as follows. For $l\in[k]$, denote:

$$a_1 = \widehat{\mathbb{P}}_{s_i(v_{i,l})},$$

$$b_1 = \mathbb{P}_{mix}(v_{i,l}) - \mu_i\widehat{\mathbb{P}}_{s_i}(v_{i,l}) - \sum_{j=1}^{i-1}\sum_{s\in S_j}\pi_s\widehat{\mathbb{P}}_s(v_{i,l}),$$

$$c = \widehat{\mathbb{P}}_{s_i}(s_i \cup s_{-i})$$

To enforce exclusion, one mixing coefficient is set to zero at a time giving a solution $(\pi_{s_i\cup\{v^1\}}, \ldots, \pi_{s_i\cup\{v^k\}})$ corresponding to interventions $(s_i\cup\{v^1\}, \ldots, s_i\cup\{v^k\})$. For every mixing coefficient that is set to 0, a candidate set of intervention tuples is provided $-\mathcal{T}=\{(s_i\cup\{v^l\}, \pi_{s_i\cup\{v^l\}}): l\in\{[k]\}$ containing the solution. For every such candidate set of intervention tuples $\mathcal{T}$, the intervention identification module 108 iterates through the tuples $(s_i\cup\{v^l\}, \pi_{s_i\cup\{v^l\}})$, and if some $\pi_{s_i\cup\{v^l\}}<0$, sets $\pi_{s_i\cup\{v^l\}}\leftarrow 0$.

The intervention identification module 108 compares the candidate sets of intervention tuples to select one as the set of intervention tuples. In some configurations, the intervention identification module 108 computes the L2 norm for each candidate set of intervention tuples, and select the candidate set of intervention tuples with the lowest L2 norm. For instance, this can comprise computing the score $r(\mathcal{T})=\|A\pi-b\|^2$ where $\pi=(\pi_{s_i\cup\{v^1\}}, \ldots, \pi_{s_i\cup\{v^k\}})$ and selecting a set of intervention tuples $\mathcal{T}$ with the smallest value of $r(\mathcal{T})$.

At the end of this process, all the intervention tuples thus obtained are collect (for all $i\in[q]$), in the set $\mathcal{T}$. To make sure that exclusion is satisfied for variable $V_{N+1}$, the excluded value of node $V_{N+1}$ is found, i.e. the value which is not present in any target in $\mathcal{T}$. If no such value exists, value v of $V_{N+1}$ which minimizes $$\sum_{i=1}^{q}\pi_{s_i\cup\{v\}}$$

is found. For each $i\in[q]$, set $\pi_{s_i\cup\{v\}}\leftarrow 0$ and then renormalize the mixing coefficients $$\pi_{s_i\cup\{v^l\}} \leftarrow (\pi_{s_i\cup\{v^l\}}\times\mu_i)/\left(\sum_{l=1}^{k}\pi_{s_i\cup\{v^l\}}\right).$$

Only \ the tuples with strictly positive mixing coefficients in $\mathcal{T}$ are kept; i.e. $\mathcal{T}\leftarrow\{(s, \pi_s)\in\mathcal{T}:]\pi_s>0\}$. Return the set $\mathcal{T}$.

Given a set of intervention tuples determined by the intervention identification module 108, the intervention assignment module 110 maps samples, from the set of samples with interventions, to interventions. Let $\mathcal{T}=\{(t_i, \pi_i)\}$ be the set of intervention tuples obtained above. For each sample $$b_j^{mix}$$

in the set of samples with interventions $\mathcal{B}_{mix}$, the intervention assignment module 110 finds the intervention $t_i$ in the set of intervention tuples $\mathcal{T}$ that maximizes the probability that the sample resulted from the intervention $t_i$; i.e.

$$\hat{P}\left(b_j^{mix} \mid do(t_i)\right).$$

The intervention assignment module 110 returns an indication that the sample $$b_j^{mix}$$

was created due to that intervention $t_i$.

The user interface (UI) module 112 of the analytics system 104 provides one or more user interfaces for interacting with the system. For instance, the UI module 112 can provide user interfaces for receiving input, such as a causal graph and sample sets, and providing output, such as an indication of a set of intervention tuples and/or assignments of individual samples to interventions. For instance, the UI module 112 can provide user interfaces to a user device, such as the user device 102. The user device 102 can be any type of computing device, such as, for instance, a personal computer (PC), tablet computer, desktop computer, mobile device, or any other suitable device having one or more processors. As shown in FIG. 1, the user device 102 includes an application 114 for interacting with the analytics system 104. The application 114 can be, for instance, a web browser or a dedicated application for providing functions, such as those described herein. Among other things, the application 114 can present the user interfaces provided by the UI module 112.

Example Methods for Identifying Interventions

With reference now to FIG. 3, a flow diagram is provided that illustrates a method 300 for determining a set of intervention tuples given a system with a single variable. The method 300 can be performed, for instance, by the intervention identification module 108 of FIG. 1. Each block of the method 300 and any other methods described herein comprises a computing process performed using any combination of hardware, firmware, and/or software. For instance, various functions can be carried out by a processor executing instructions stored in memory. The methods can also be embodied as computer-usable instructions stored on computer storage media. The methods can be provided by a standalone application, a service or hosted service (standalone or in combination with another hosted service), or a plug-in to another product, to name a few.

As shown at block 302, input is received, including a causal graph, a set of baseline samples, and a set of samples with interventions. Estimated probability distributions are determined using the set of baseline samples and set of samples with interventions, as shown at block 304. In order to ensure positivity, the estimated probability distributions are perturbed to provide that all estimated probabilities are non-zero, as shown at block 306. This can include adding a small constant to any estimated probabilities that are not non-zero and renormalizing the estimated probability distributions.

Candidate sets of interventions tuples are determined using the estimated probability distributions, as shown at block 308. As described hereinabove, this can include generating a system of equations and using the estimated probabilities to determine mixing coefficients for interventions. Enforcing exclusion, each mixing coefficient is set to zero one at a time, and the system of equations is solved using the probability estimates to determine the values of the mixing coefficients. This provides multiple candidate sets of intervention tuples—a set for each mixing coefficient being set to zero. In some configurations, any non-zero mixing coefficient is set to zero. Additionally, if a threshold is employed, any mixing coefficient below the threshold can be set to zero, and the remaining coefficients above the threshold can be renormalized.

As shown at block 310, the candidate sets of interventions tuples are compared, and one is selected as the set of intervention tuples. In some instances, this comprises computing the L2 norm for each candidate set of intervention tuples and selecting the candidate set of intervention tuples with the lowest L2 norm.

Figure 4:
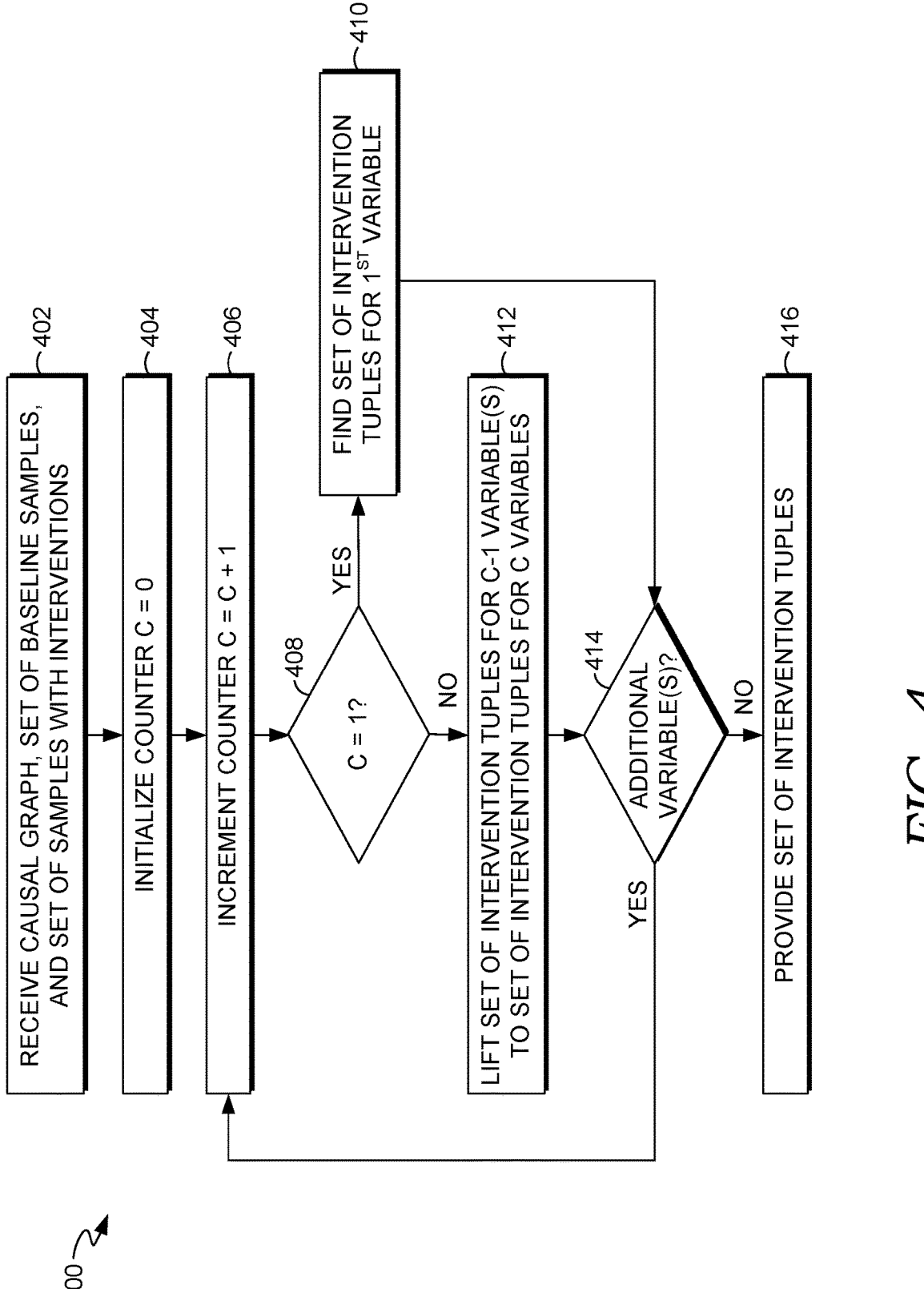
FIG. 4 is a flow diagram showing a method for determining a set of intervention tuples given multiple variables in accordance with some implementations of the present disclosure.

Turning now to FIG. 4, a flow diagram is provided showing a method 400 for determining a set of intervention tuples given a system with multiple variables. As shown at block 402, input is received, including a causal graph, a set of baseline samples, and a set of samples with interventions. The process involves iteratively determining a set of invention tuples for N variables and lifting the solution to N+1 variables.

A counter is initialized to zero, as shown at block 404, and the counter is incremented by one at block 406. A determination is made at block 408 whether the counter is equal to one. Because the counter is initially at one, a first variable is selected from the causal graph, and a set of intervention tuples is determined for the first variable, as shown in block 410. The first variable selected here can be based on the topological ordering of variables from the causal graph. For instance, using the causal graph 200 of FIG. 2, the Past_Opens variable 202 can be initially selected. The set of invention tuples determined at block 410 is for a single variable, for instance, using an approach similar to that described above with reference to the method 300 of FIG. 3. However, the process would involve marginalizing data from the set of baseline samples and the set of samples with interventions to determine estimated probability distributions. For example with reference again to the causal graph 200 of FIG. 2, estimated probability distributions can initially be determined for the Past_Opens variable 202 and used to determine the set of intervention tuples for that single variable.

Post this, a determination is performed at block 414 regarding whether there are any additional variables. If there are additional variable(s), the process returns to block 406, at which the counter is incremented by one. Because the counter is no longer at one, the process continues from block 408 to block 412, at which the solution of the set of intervention tuples for C−1 variables (i.e., N variables) is lifted to a solution of a set of intervention tuples for C variables (i.e., N+1 variables). When the counter is at two, the single variable provided in block 410 is lifted for the second variable at block 412. As described hereinabove, this can include solving a system of equations using the set of intervention tuples determined for the Pt variable and probability distributions determined for the 2nd variables (which can require marginalizing the data if the total number of variables is greater than the current N+1 variables). To enforce exclusion, each mixing coefficient is set to zero one at a time, and the system of equations is solved to determine the values of the mixing coefficients. This provides multiple candidate sets of intervention tuples—a set for each mixing coefficient being set to zero. In some configurations, any non-zero mixing coefficient can be set to zero. Additionally, if a threshold is employed, any mixing coefficient below the threshold can be set to zero, and the remaining coefficients above the threshold can be renormalized. The candidate sets of interventions tuples are compared, and one is selected as the set of intervention tuples for the 2nd variables. In some instances, this can comprise computing the L2 norm for each candidate set of intervention tuples and selecting the candidate set of intervention tuples with the lowest L2 norm.

As shown at block 414, a determination is made regarding whether there are any additional variables. If so, the process of blocks 406 through 412 is repeated. In particular, the determination of intervention tuple set with C equal to $(N+1)^{th}$ variable is made using the intervention tuple set found in block 412 when C was equal to N. The variable selected at each iteration can be based on the topological ordering of variables from the causal graph. As an example using the causal graph 200 of FIG. 2, after computing the set of intervention tuples for two variables (i.e., for the Past_Opens variable 202 and the Treatment variable 204), the C variables selected at block 412 would include all three variables—i.e., the Past_Opens variable 202, the Treatment variable 204, and the Open variable 206. The set of intervention tuples for N+1 variables determined at block 412 for the current iteration comprises the set of intervention tuples from the previous iteration (e.g., the set of intervention tuples determined for the Past_Opens variable 202 and the Treatment variable 204). That set of intervention tuples for N variables is then lifted to a set of intervention tuples for N+1 variables. For instance, the set of intervention tuples determined for the Past_Opens variable 202 and the Treatment variable 204 would be lifted to a set of intervention tuples for the Past_Opens variable 202, the Treatment variable 204, and the Open variable 206. Once it is determined at block 414 that no additional variables remain, a final set of intervention tuples is provided, as shown at block 416.

Figure 5:
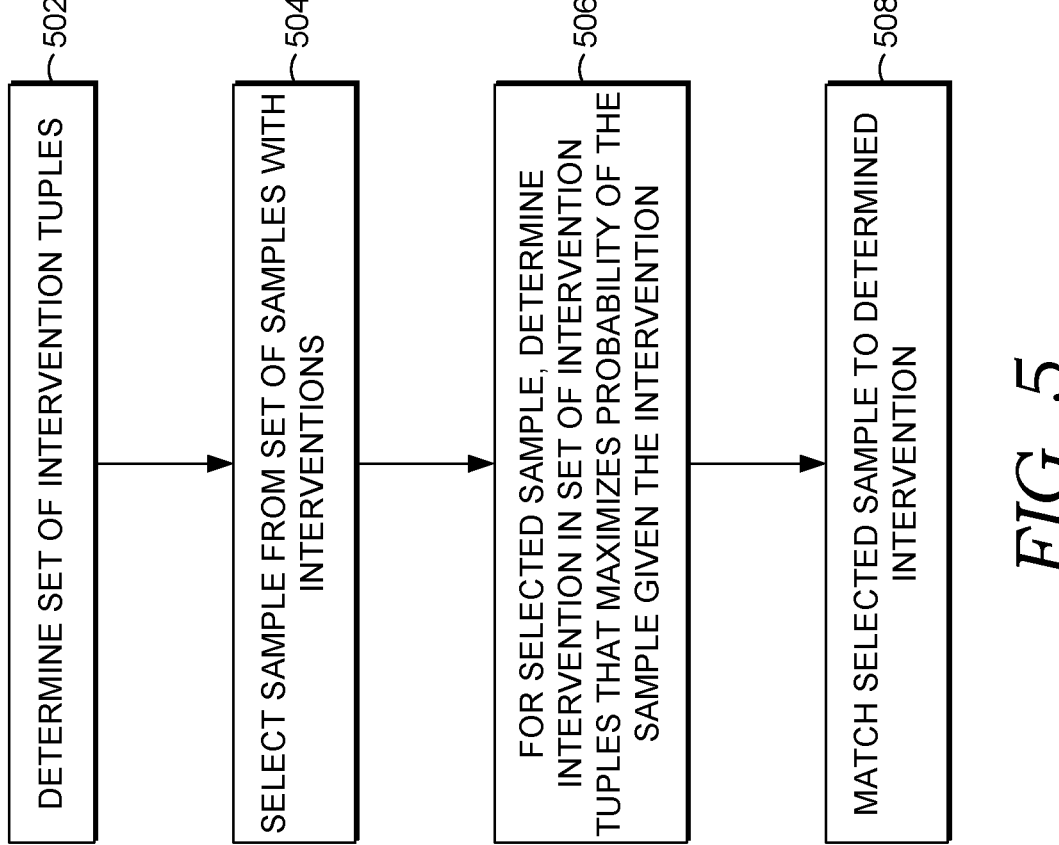
FIG. 5 is a flow diagram showing a method for matching individual samples to interventions in accordance with some implementations of the present disclosure.

With reference now to FIG. 5, a flow diagram is provided that shows a method 500 for matching a sample, from the set of samples with interventions, to an intervention. The method 500 can be performed on any number of samples from the set of samples with interventions. As shown at block 502, a set of intervention tuples is determined. For instance, the method 300 of FIG. 3 or the method 400 of FIG. 4 can be employed to provide the set of intervention samples. Additionally, as shown at block 504, a sample from the set of samples with interventions is selected.

As shown at block 506, an intervention, from the set of intervention tuples, that maximizes the probability that the sample resulted from the intervention is determined. The sample is matched to the determined intervention, as shown at block 508.

Performance Evaluation

Two experiments were run to assess the performance of the technology described herein. In the first experiment, the approach of the technology described herein was compared to a brute force baseline on a small graph (since brute force does not scale) using accuracy metrics. In the second experiment, random causal graphs were simulated, samples were generated from the causal graphs, and the performance of the technology described herein was evaluated using accuracy metrics. Note that these experiments are focused on comparing the performance of recovering the set of intervention tuples of the original mixture. The experiments do not compare the performance of the final sample to intervention mapping since it depends on the previous step and the more accurate the identification of intervention tuples, the more accurate the mapping will be. Basically, the errors introduced are mostly due to the algorithm that finds the intervention tuples, and the error from mapping of samples to interventions is essentially due to noise from sampling.

Comparison with Brute Force Baseline:

Note that the brute force algorithm will only work for very small number of nodes. A causal graph on 4 nodes was generated with each node having 4 categories, creating an input mixture with 16 intervention components. 10000 samples were obtained from both the actual model and the mixture, the two algorithms (i.e., the technology described herein and brute force) were applied to these samples. Since samples are being used, both the algorithms will find non-zero mixing coefficients for components and therefore to correctly identify the unknown interventions a threshold was applied to the mixing proportions. To have a fair comparison between the algorithms, the same threshold 0.001 was used. Table 1 below compares some accuracy metrics of both these algorithms. Recall is the number of interventions that were correctly identified. Precision is the fraction of correct interventions among the ones recovered. RMSE is the root mean squared error in the mixing proportions. Note that for even slightly larger graphs, the brute force will not be tractable and the algorithm of the current technology will be the only known one that is efficient.

TABLE 1

| Performance comparison | | |
| --- | --- | --- |
| | Brute Force | Current Technology |
| Recall | 0.94 | 0.94 |
| Precision | 0.33 | 0.76 |
| RMSE | 0.027 | 0.018 |

Performance for Larger Graphs and Varying Sample Sizes.

A simulation study was performed to experimentally analyze performance of the technology described herein. Simulation Setup.

For each simulation setting (N=number of nodes, M=number of samples), a directed acyclic graph was sampled on N nodes (each having 3 categories), from the Scale-Free (SF) model, with number of edges chosen uniformly randomly from [N, 5N]. For each graph, the CPD of each node was modeled as a multinoulli distribution with Dirichlet priors having fixed parameter $\alpha=2$ for all categories. This was done to conform with positivity. This generated a causal Bayesian Network $\mathcal{G}$. A set $\mathcal{B}$ of M samples was generated using ancestral sampling on this network and used as input for an algorithm using the technology described herein. To create a mixture, an integer m was uniformly randomly chosen from the set [4,16] and used as the number of interventions in the mixture. Iterating from 1 to m was performed to build each intervention target of the mixture. First, the size of the target was chosen by picking an integer r uniformly randomly from the set $\{0, \ldots, N\}$. Then, an r—sized subset of [N] was uniformly randomly chosen, defining variables in the target. For each of these variables, a category was uniformly randomly chosen and removed from consideration (to satisfy exclusion). From the remaining categories, one was uniformly randomly selected for each variable in the target and used to define the intervention. Finally, m scalar weights were generated for mixing coefficients such that they sum to 1. To make sure that these mixing coefficients are not too small, there were generated with Dirichlet priors with all parameter values fixed to 2. A set $\mathcal{B}_{mix}$ containing M samples was generated from this mixture model and used as input for the algorithm. Parameters $\in$, $\delta$ used by the algorithm were set to 0.01 and 1/M respectively. The settings for N and M used in the

17

18 experiments were $(N, M) \in \{4,8,12\} \times \{2^4, 2^5, \ldots, 2^{20}\}$ where $\times$ is the direct product of sets.

Evaluation Metrics:

Let $\mathcal{T}$ denote the actual set of intervention targets and $\hat{\mathcal{T}}$ denote the set of intervention targets computed by the algorithm of the technology described herein. Let $\pi_t$, $\hat{\pi}_s$ denote mixing coefficients of target t, s in $\mathcal{T}$ and $\hat{\mathcal{T}}$ respectively. The following evaluation metrics were used to evaluate the performance of the algorithm.

1. Recall: Proportion of number of targets in $\mathcal{T}$ that were correctly identified in $\hat{\mathcal{T}}$ $$\text{Recall} = \frac{|\mathcal{T} \cap \hat{\mathcal{T}}|}{|\mathcal{T}|}$$

2. Root Mean Squared Error: Root-mean-squared error (RMSE) in the mixing coefficients.

$$RMSE = \sqrt{\frac{\sum_{t \in \mathcal{T} \cap \hat{\mathcal{T}}} (\pi_t - \hat{\pi}_t)^2 + \sum_{t \in (\mathcal{T} \setminus \hat{\mathcal{T}})} (\pi_t)^2 + \sum_{t \in (\hat{\mathcal{T}} \setminus \mathcal{T})} (\hat{\pi}_t)^2}{|\mathcal{T} \cup \hat{\mathcal{T}}|}}$$

3. False-Positive RMSE: RMSE in the mixing coefficients of the incorrectly identified targets.

$$FP-RMSE = \sqrt{\frac{\sum_{t \in (\hat{\mathcal{T}} \setminus \mathcal{T})} (\hat{\pi}_t)^2}{|\hat{\mathcal{T}} \setminus \mathcal{T}|}}$$

4. False-Negative RMSE: RMSE in the mixing coefficients of targets not identified.

$$FN-RMSE = \sqrt{\frac{\sum_{t \in (\mathcal{T} \setminus \hat{\mathcal{T}})} (\pi_t)^2}{|\mathcal{T} \setminus \hat{\mathcal{T}}|}}$$

Figure 6A:
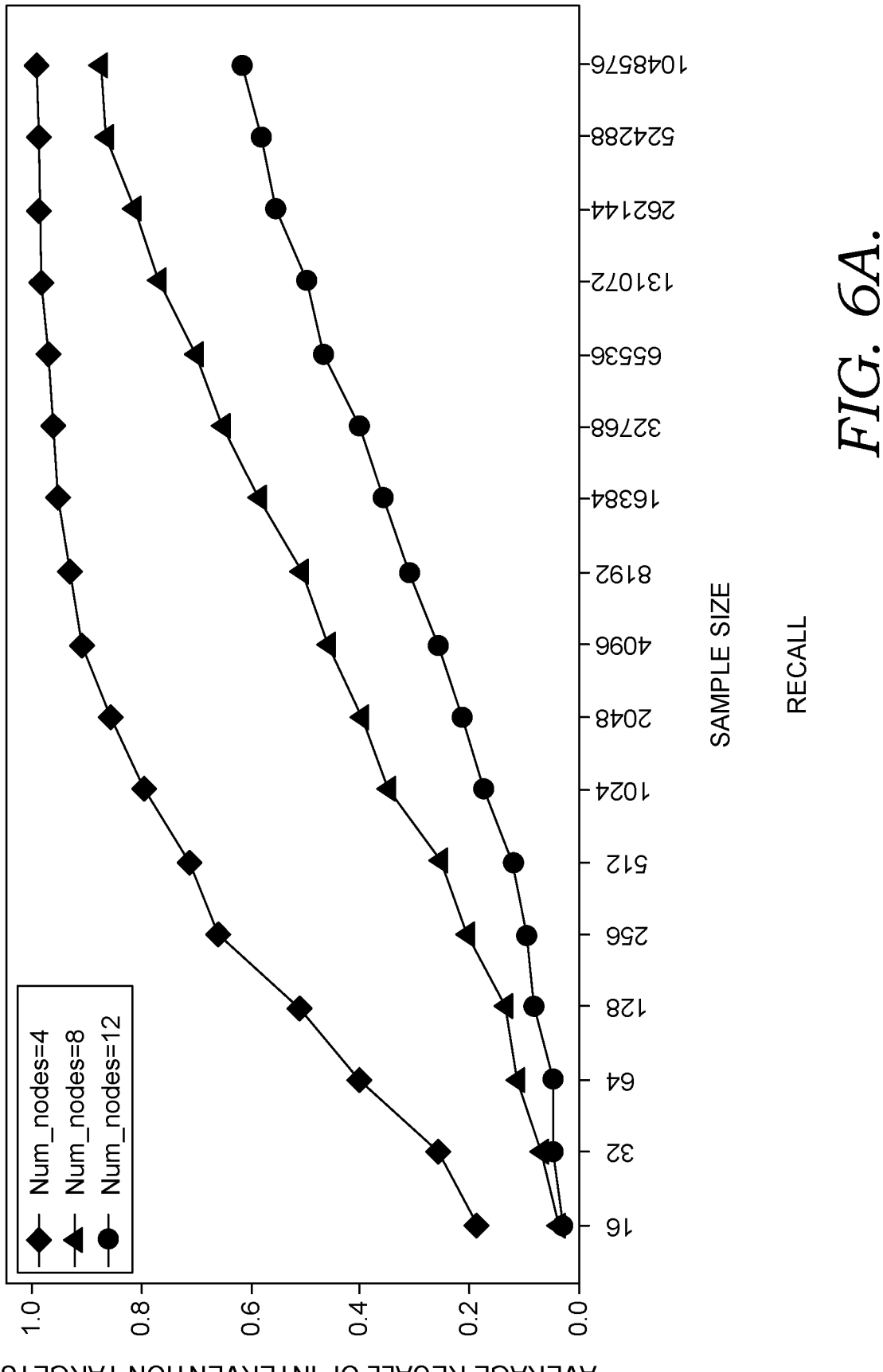
FIGS. 6A-6D are plots that demonstrate performance of the algorithm of the technology described herein as sample size varies.

Results Discussion:

FIGS. 6A-6D presents four plots that demonstrate performance of the algorithm of the technology described herein as sample size M varies in $\{2^4, 2^5, \ldots, 2^{20}\}$. The number of nodes N was also varied in $\{4,8,12\}$ and separate plots are shown for each N in each of the figures. The four plots in FIGS. 6A-6D, demonstrate four different accuracy metrics described above. In FIG. 6A, the average recall of intervention targets is plotted as M increases. Recall for a single input instance is the number of intervention targets in the input that are identified in the output. Average recall is the average of this over all random instances generated in the simulation. A general trend of increase in the recall is observed as the number of samples is increased. Also, a relatively larger number of samples were required to achieve the same level of recall for mixtures generated from CBN with a large number of nodes as compared to smaller ones. This trend is expected as the algorithm estimates the interventions by sequentially adding nodes to them. Hence, for larger-sized CBNs, the error accumulated is larger as compared to smaller ones.

Figure 6B:
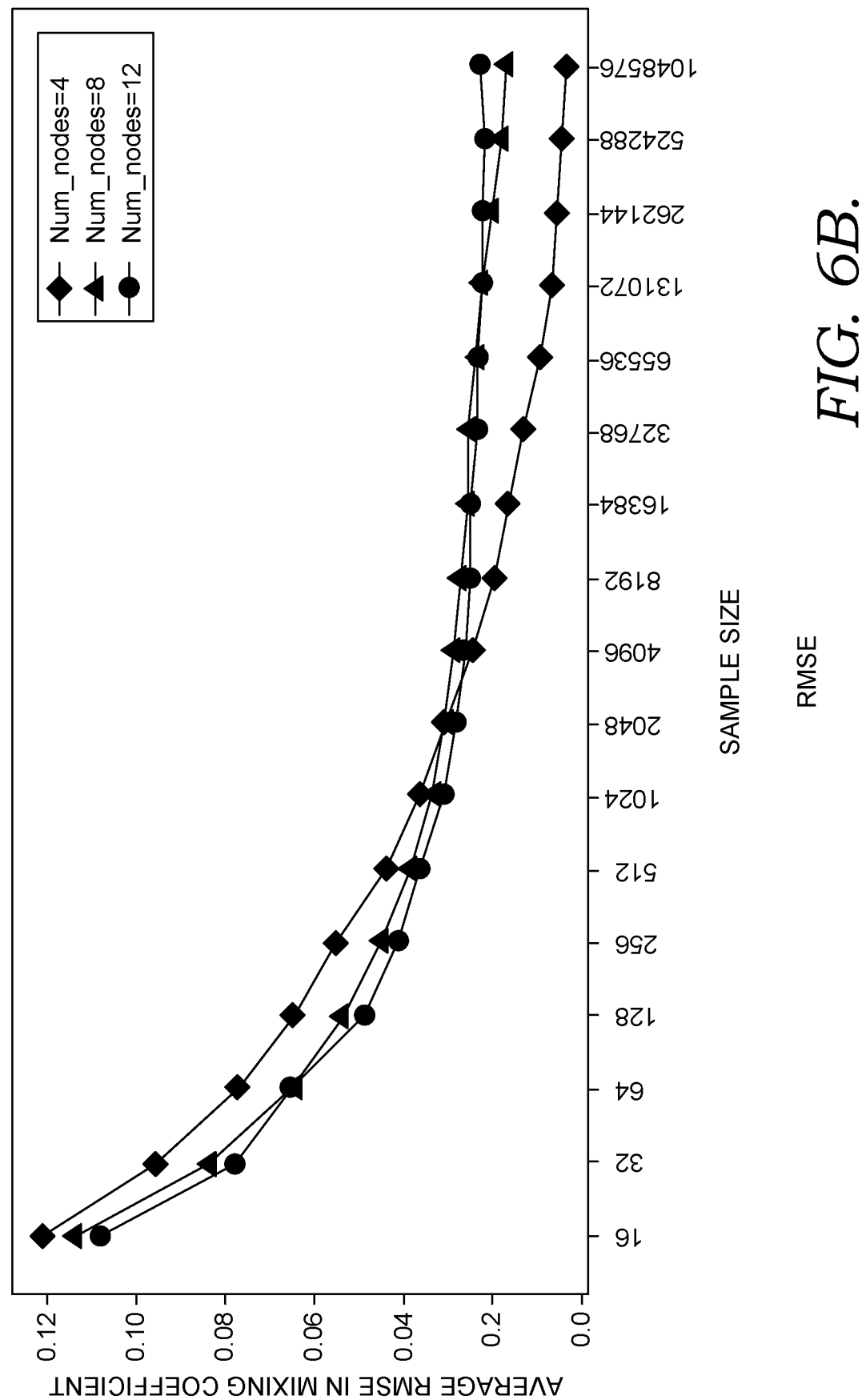

In FIG. 6B, the average root-mean-squared error (RMSE) between the estimated and actual mixing coefficients is plotted. For each input, RMSE was calculated using the definition supplied above. Then it was averaged over all the random input instances. A fast decrease in the average RMSE was observed as M increases. It was also observed that the average RMSE is higher for higher N. This is also expected since for distributions on larger number of variables, more samples will be needed to estimate marginal probabilities accurately.

Figure 6C:
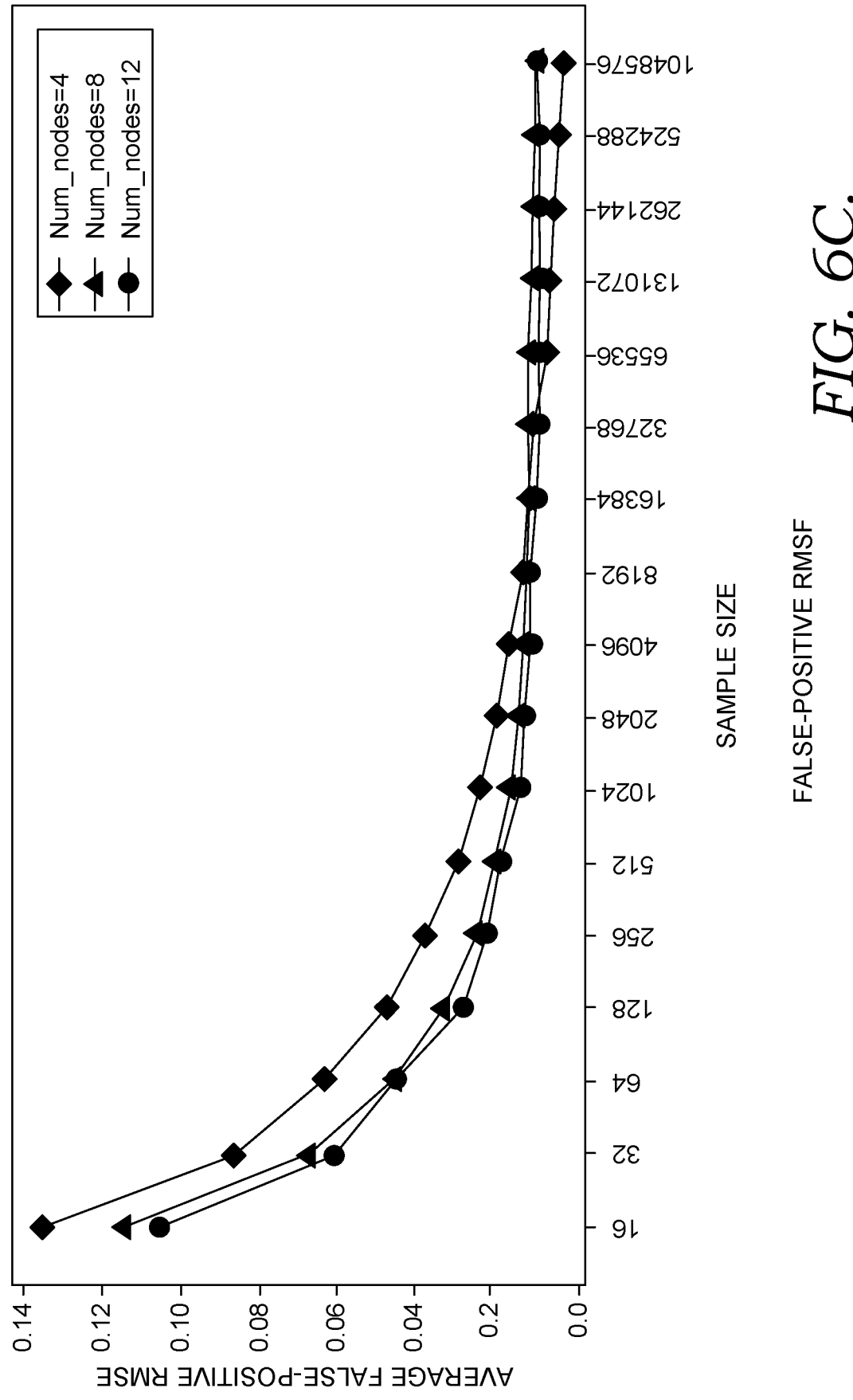

In FIG. 6C, average False-Positive RMSE or FP-RMSE is plotted as M increases. For each input instance, FP-RMSE computes the RMSE in mixing proportions for components which are not present in actual target set but predicted by our algorithm. This was then averaged over all the random input instances. For each value of N, a similar decreasing trend in this plot was observed showing that incorrect targets in the output have very small mixing proportions (as sample size increases) and therefore even if they are present in the output their contribution is insignificant.

Figure 6D:
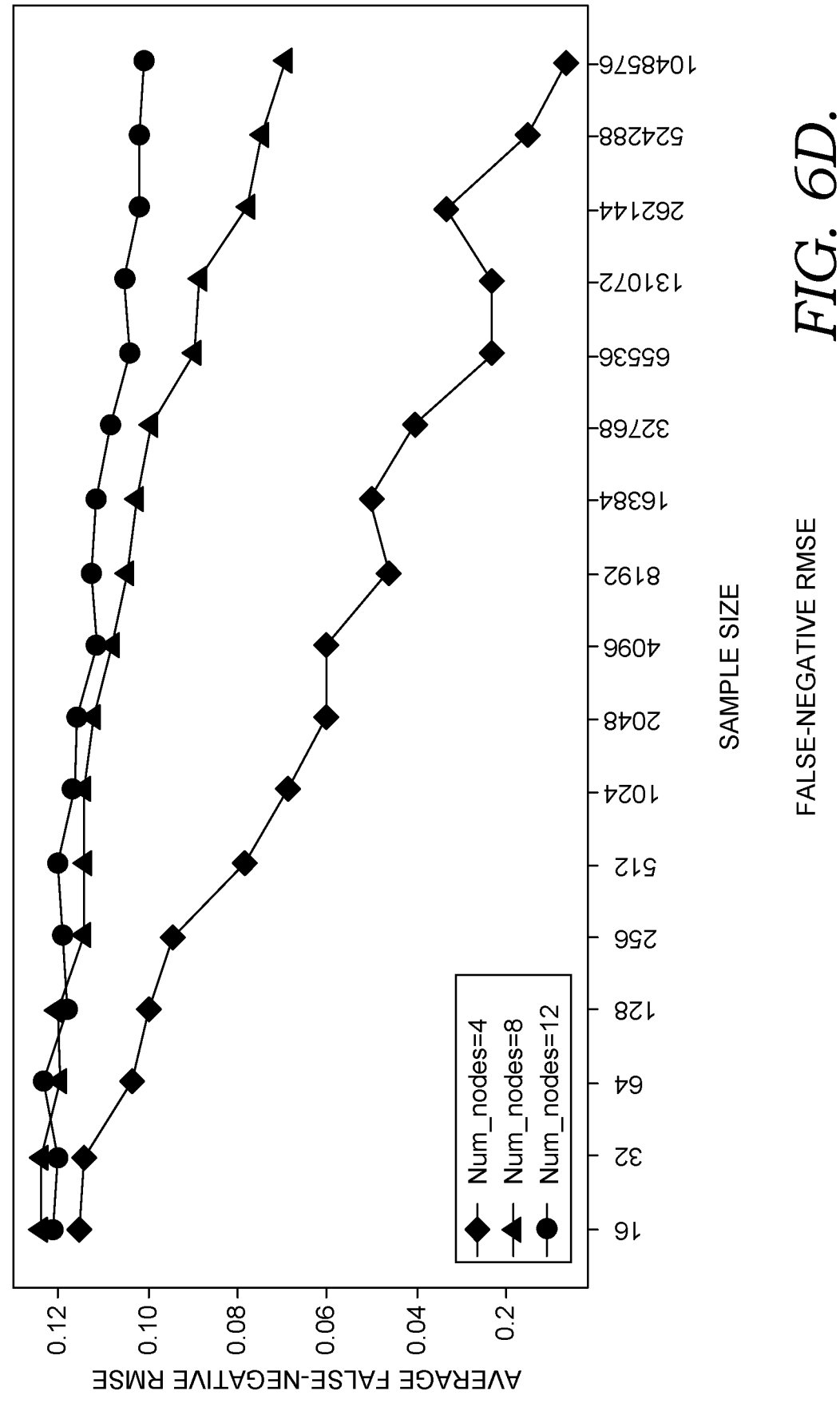

In FIG. 6D, average False-Negative RMSE or FN-RMSE is plotted as M increases. For each input instance, FN-RMSE computes the RMSE in mixing proportions for components present in the actual target but not present in the output targets. This was then averaged over all the random input instances. Even though a decreasing trend was observed in this situation as well, the rate is much slower as N increases. This implies that the sample complexity of the algorithm is high and it might need too many samples to correctly identify the coefficients of interventions present in the input.

Figure 7A:
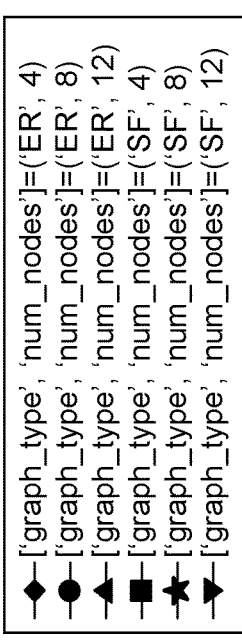
FIGS. 7A-7B are plots that demonstrate and compare performance of the technology described herein as the number of nodes and samples increase.
Figure 7B:
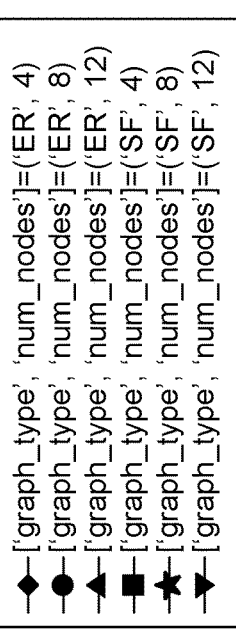

FIGS. 7A-7B demonstrate and compare performance of the technology described herein as M, N increase, for CBNs generated using different random graph models (Scale-Free and Erdos-Renyi). No significant difference in performance was observed suggesting that only high level graph parameters (such as number of nodes, edges, in-degree etc.) can be having an impact on performance and the topology (given these parameters) might not be that crucial.

Figure 8A:
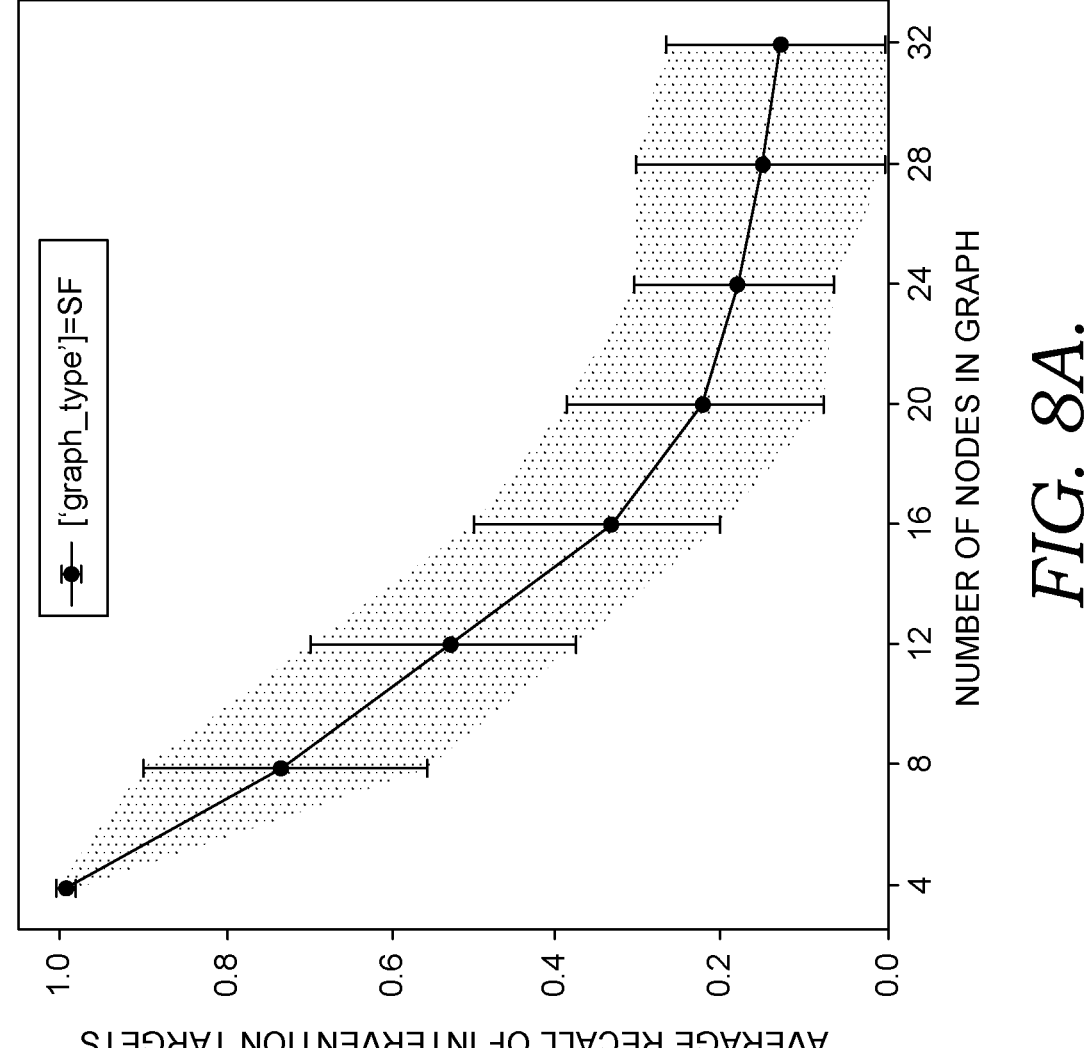
FIGS. 8A-8B are plots that demonstrate performance of the technology described herein as number of nodes varies, for a fixed sample size.
Figure 8B:
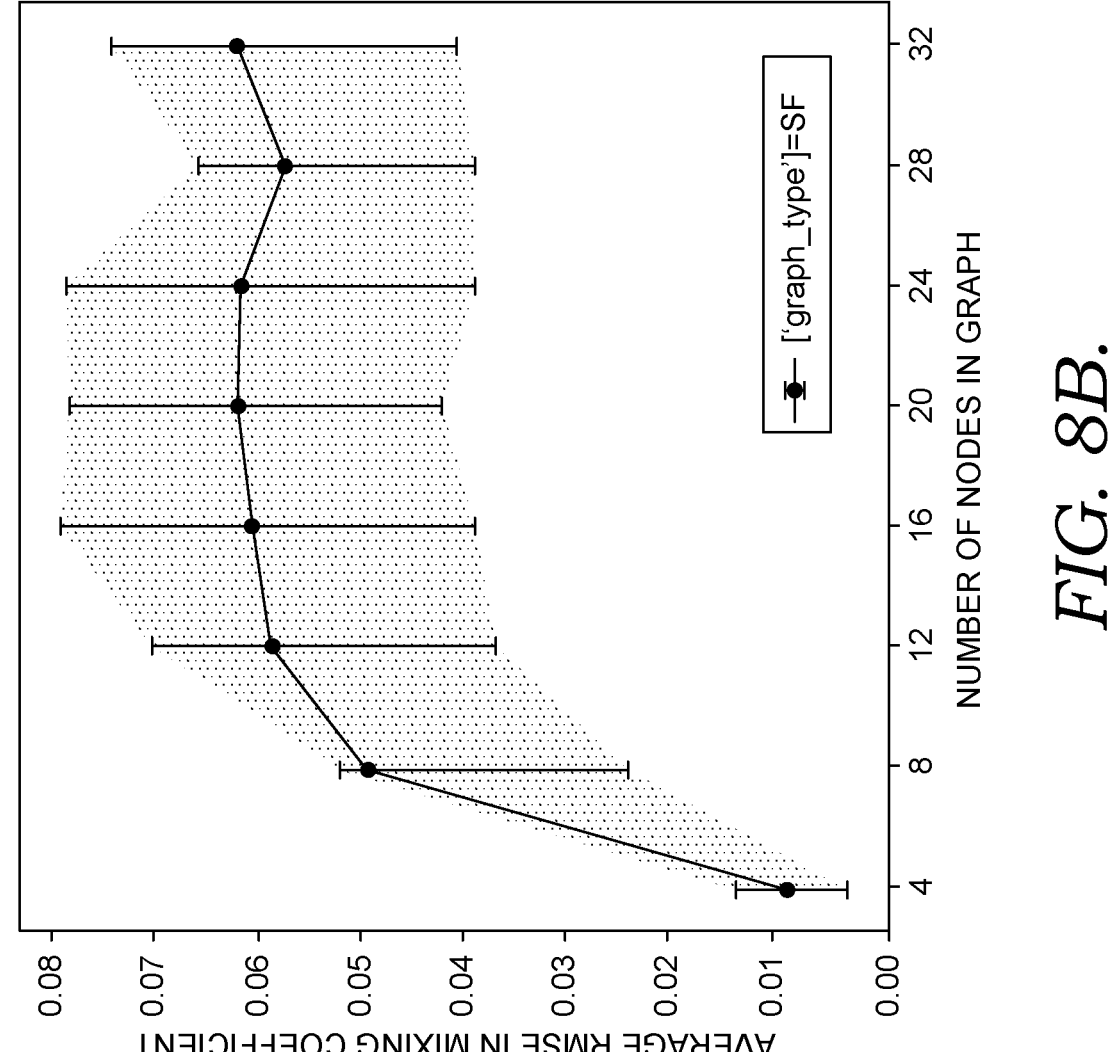

To further understand the performance of the technology described herein with respect to the number of nodes, in FIGS. 8A-8B, the Average Recall and Average RMSE are plotted as number of nodes varies from 4 to 32, for a fixed sample size of $\sim 10^6$. It is observed that recall decreases and RMSE increases very quickly as number of nodes increase. Even though this is expected since error is accumulated as nodes are successively added and new interventions found, such performance for a very large sample size indicates dependence of sample complexity on the number of nodes.

Exemplary Operating Environment

Figure 9:
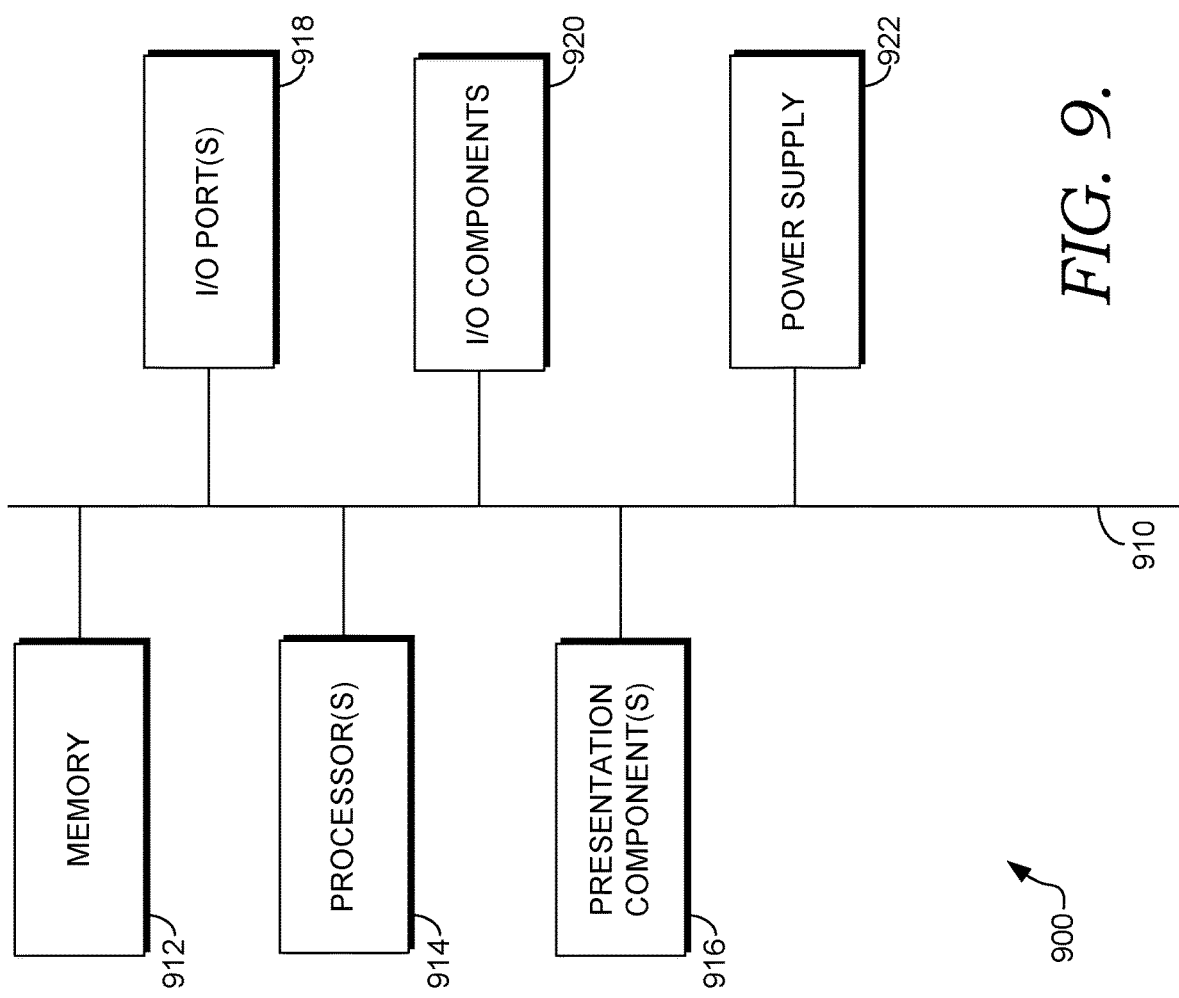
FIG. 9 is a block diagram of an exemplary computing environment suitable for use in implementations of the present disclosure.

Having described implementations of the present disclosure, an exemplary operating environment in which embodiments of the present invention can be implemented is described below in order to provide a general context for various aspects of the present disclosure. Referring initially to FIG. 9 in particular, an exemplary operating environment for implementing embodiments of the present invention is shown and designated generally as computing device 900. Computing device 900 is but one example of a suitable computing environment and is not intended to suggest any limitation as to the scope of use or functionality of the invention. Neither should the computing device 900 be interpreted as having any dependency or requirement relating to any one or combination of components illustrated.

The invention can be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The invention can be practiced in a variety of system configurations, including hand-held devices, consumer electronics, general-purpose computers, more specialty computing devices, etc. The invention can also be practiced in distributed computing environments where tasks are performed by remote-processing devices that are linked through a communications network.

With reference to FIG. 9, computing device 900 includes bus 910 that directly or indirectly couples the following devices: memory 912, one or more processors 914, one or more presentation components 916, input/output (I/O) ports 918, input/output components 920, and illustrative power supply 922. Bus 910 represents what can be one or more busses (such as an address bus, data bus, or combination thereof). Although the various blocks of FIG. 9 are shown with lines for the sake of clarity, in reality, delineating various components is not so clear, and metaphorically, the lines would more accurately be grey and fuzzy. For example, one can consider a presentation component such as a display device to be an I/O component. Also, processors have memory. The inventors recognize that such is the nature of the art, and reiterate that the diagram of FIG. 9 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 9 and reference to "computing device."

Computing device 900 typically includes a variety of computer-readable media. Computer-readable media can be any available media that can be accessed by computing device 900 and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 912 includes computer storage media in the form of volatile and/or nonvolatile memory. The memory can be removable, non-removable, or a combination thereof. Exemplary hardware devices include solid-state memory, hard drives, optical-disc drives, etc. Computing device 900 includes one or more processors that read data from various entities such as memory 912 or I/O components 920. Presentation component(s) 916 present data indications to a user or other device. Exemplary presentation components include a display device, speaker, printing component, vibrating component, etc.

I/O ports 918 allow computing device 900 to be logically coupled to other devices including I/O components 920, some of which can be built in. Illustrative components include a microphone, joystick, game pad, satellite dish, scanner, printer, wireless device, etc. The I/O components 920 can provide a natural user interface (NUI) that processes air gestures, voice, or other physiological inputs generated by a user. In some instance, inputs can be transmitted to an appropriate network element for further processing. A NUI can implement any combination of speech recognition, touch and stylus recognition, facial recognition, biometric recognition, gesture recognition both on screen and adjacent to the screen, air gestures, head and eye-tracking, and touch recognition associated with displays on the computing device 900. The computing device 900 can be equipped with depth cameras, such as, stereoscopic camera systems, infrared camera systems, RGB camera systems, and combinations of these for gesture detection and recognition. Additionally, the computing device 900 can be equipped with accelerometers or gyroscopes that enable detection of motion.

The present invention has been described in relation to particular embodiments, which are intended in all respects to be illustrative rather than restrictive. Alternative embodiments will become apparent to those of ordinary skill in the art to which the present invention pertains without departing from its scope.

Having identified various components utilized herein, it should be understood that any number of components and arrangements can be employed to achieve the desired functionality within the scope of the present disclosure. For example, the components in the embodiments depicted in the figures are shown with lines for the sake of conceptual clarity. Other arrangements of these and other components can also be implemented. For example, although some components are depicted as single components, many of the elements described herein can be implemented as discrete or distributed components or in conjunction with other components, and in any suitable combination and location. Some elements can be omitted altogether. Moreover, various functions described herein as being performed by one or more entities can be carried out by hardware, firmware, and/or software, as described below. For instance, various functions can be carried out by a processor executing instructions stored in memory. As such, other arrangements and elements (e.g., machines, interfaces, functions, orders, and groupings of functions) can be used in addition to or instead of those shown.

Embodiments described herein can be combined with one or more of the specifically described alternatives. In particular, an embodiment that is claimed can contain a reference, in the alternative, to more than one other embodiment. The embodiment that is claimed can specify a further limitation of the subject matter claimed.

The subject matter of embodiments of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" can be used herein to connote different elements of methods employed, the terms should not be interpreted as implying any particular order among or between various steps herein disclosed unless and except when the order of individual steps is explicitly described.

For purposes of this disclosure, the word "including" has the same broad meaning as the word "comprising," and the word "accessing" comprises "receiving," "referencing," or "retrieving." Further, the word "communicating" has the same broad meaning as the word "receiving," or "transmitting" facilitated by software or hardware-based buses, receivers, or transmitters using communication media described herein. In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

For purposes of a detailed discussion above, embodiments of the present invention are described with reference to a distributed computing environment; however, the distributed computing environment depicted herein is merely exemplary. Components can be configured for performing novel embodiments of embodiments, where the term "configured for" can refer to "programmed to" perform particular tasks or implement particular abstract data types using code. Further, while embodiments of the present invention can generally refer to the technical solution environment and the schematics described herein, it is understood that the techniques described can be extended to other implementation contexts.

From the foregoing, it will be seen that this invention is one well adapted to attain all the ends and objects set forth above, together with other advantages which are obvious and inherent to the system and method. It will be understood that certain features and subcombinations are of utility and can be employed without reference to other features and subcombinations. This is contemplated by and is within the scope of the claims.

What is claimed is:

1. A computerized method comprising:

receiving, by one or more processors, (i) a causal graph defining causal relationships among a plurality of variables, (ii) a set of baseline samples drawn from a baseline distribution associated with the causal graph, and (iii) a set of samples drawn from a mixture distribution corresponding to a mixture of interventions affecting at least a portion of the set of samples;

estimating, by one or more processors, from the set of baseline samples and the set of samples drawn from the mixture distribution, one or more probability distributions over subsets of the plurality of variables;

enforcing, by one or more processors, positivity on the one or more probability distributions by perturbing at least one of the one or more probability distributions such that probabilities in the at least one of the one or more probability distributions are non-zero;

iteratively determining, by the one or more processors, a final set of intervention tuples for the plurality of variables from the causal graph, each intervention tuple identifying (i) an intervention that sets one or more variables to respective values and (ii) a mixing coefficient representing a fraction of the set of samples drawn from the mixture distribution attributable to the intervention, the iteratively determining comprising:

selecting variables from the causal graph for a current iteration based on a topological ordering of the causal graph, determining a set of intervention tuples for N variables by forming a system of equations using the one or more probability distributions and enforcing exclusion by repeatedly setting a mixing coefficient to zero to generate a plurality of candidate sets of intervention tuples, lifting the set of intervention tuples for the N variables to a set of invention intervention tuples for N+1 variables using (i) the set of intervention tuples for the N variables and (ii) estimated probability distributions for the N+1 variables, pruning intervention tuples having mixing coefficients below a threshold and renormalizing remaining mixing coefficients, and repeating the selecting, determining, lifting, and applying by incrementing N until the final set of intervention tuples is generated for the plurality of variables;

assigning, by the one or more processors, each sample from at least a portion of the set of samples with interventions to an intervention using the final set of intervention tuples; and storing, in computer memory, an association between (i) sample identifiers for the portion of the set of samples and (ii) respective assigned interventions to provide a labeled dataset for a causal analytics process.

2. The computerized method of claim 1, wherein determining the set of intervention tuples for a first variable at a first iteration comprises:

generating estimated probability distributions for the first variable by marginalizing data from the set of baseline samples and the set of samples with interventions;

generating a first system of equations to determine mixing coefficients for interventions for the first variable;

generating a first plurality of candidate sets of intervention tuples for the first variable by repeatedly setting each mixing coefficient in the first system of equations to zero and solving the first system of equations using the estimated probability distributions for the first variable; and selecting the set of intervention tuples for the first variable from the first plurality of candidate sets of intervention tuples.

3. The computerized method of claim 2, wherein generating the estimated probability distributions for the first variable includes perturbing the estimated probability distributions such that all probabilities are non-zero.

4. The computerized method of claim 2, wherein a first mixing coefficient for a first intervention tuple in the set of intervention tuples for the first variable is set to zero based on the first mixing coefficient being below a threshold and other mixing coefficients are renormalized based on setting the first mixing coefficient to zero.

5. The computerized method of claim 2, wherein the set of intervention tuples for the first variable is selected from the first plurality of candidate sets of intervention tuples by:

computing an L2 norm for each candidate set of intervention tuples; and selecting a candidate set of intervention tuples with a lowest L2 norm.

6. The computerized method of claim 2, wherein determining the set of intervention tuples for the first variable and a second variable at the first iteration comprises:

generating estimated probability distributions for the first variable and the second variable using the set of baseline samples and the set of samples with interventions;

generating a second system of equations to determine mixing coefficients for interventions for the first variable and the second variable;

generating a second plurality of candidate sets of intervention tuples for the first variable and the second variable by repeatedly setting each mixing coefficient in the second system of equations to zero and solving the second system of equations using the set of intervention tuples for the first variable and the estimated probability distributions for the first variable and the second variable; and selecting the set of intervention tuples for the first variable and the second variable from the second plurality of candidate sets of intervention tuples.

7. The computerized method of claim 6, wherein determining the set of intervention tuples for the first variable, the second variable, and a third variable at a second iteration comprises:

generating estimated probability distributions for the first variable, the second variable, and the third variable using the set of baseline samples and the set of samples with interventions;

generating a third system of equations to determine mixing coefficients for interventions for the first variable, the second variable, and the third variable;

generating a third plurality of candidate sets of intervention tuples for the first variable, the second variable, and the third variable by repeatedly setting each mixing coefficient in the third system of equations to zero and solving the third system of equations using the set of intervention tuples for the first variable and the second variable and the estimated probability distributions for the first variable, the second variable, and the third variable; and selecting the set of intervention tuples for the first variable, the second variable, and the third variable from the third plurality of candidate sets of intervention tuples.

8. One or more computer storage media storing computer-useable instructions that, when used by a computing device, cause the computing device to perform operations, the operations comprising:

receiving (i) a causal graph defining causal relationships among a plurality of variables, (ii) a set of baseline samples drawn from a baseline distribution associated with the causal graph, and (iii) a set of samples drawn from a mixture distribution corresponding to a mixture of interventions affecting at least a portion of the set of samples;

estimating, from the set of baseline samples and the set of samples drawn from the mixture distribution, one or more probability distributions over subsets of the plurality of variables;

enforcing positivity on the one or more probability distributions by perturbing at least one of the one or more probability distributions such that probabilities in the at least one of the one or more probability distributions are non-zero;

iteratively determining a final set of intervention tuples for the plurality of variables from the causal graph, each intervention tuple identifying (i) an intervention that sets one or more variables to respective values and (ii) a mixing coefficient representing a fraction of the set of samples drawn from the mixture distribution attributable to the intervention, the iteratively determining comprising:

selecting variables from the causal graph for a current iteration based on a topological ordering of the causal graph, determining a set of intervention tuples for N variables by forming a system of equations using the one or more probability distributions and enforcing exclusion by repeatedly setting a mixing coefficient to zero to generate a plurality of candidate sets of intervention tuples, lifting the set of intervention tuples for the N variables to a set of intervention tuples for N+1 variables using (i) the set of intervention tuples for the N variables and (ii) estimated probability distributions for the N+1 variables, pruning intervention tuples having mixing coefficients below a threshold and renormalizing remaining mixing coefficients, and repeating the selecting, determining, lifting, and applying by incrementing N until the final set of intervention tuples is generated for the plurality of variables;

assigning each sample from at least a portion of the set of samples with interventions to an intervention using the final set of intervention tuples; and storing, in computer memory, an association between (i) sample identifiers for the portion of the set of samples and (ii) respective assigned interventions to provide a labeled dataset for a causal analytics process.

9. The one or more computer storage media of claim 8, wherein determining the set of intervention tuples for a first variable at a first iteration comprises generating estimated probability distributions for the first variable that includes perturbing the estimated probability distributions such that all probabilities are non-zero.

10. The one or more computer storage media of claim 9, wherein a first mixing coefficient for a first intervention tuple in the selected set of intervention tuples for the first variable is set to zero based on the first mixing coefficient being below a threshold and other mixing coefficients are renormalized based on setting the first mixing coefficient to zero.

11. The one or more computer storage media of claim 9, wherein the set of intervention tuples for the first variable is selected from a first plurality of candidate sets of intervention tuples for the first variable by:

computing an L2 norm for each candidate set of intervention tuples; and selecting a candidate set of intervention tuples with a lowest L2 norm.

12. The one or more computer storage media of claim 9, wherein;

generating estimated probability distributions for the first variable and a second variable from the causal graph using the set of baseline samples and the set of samples with interventions;

generating a second system of equations to determine mixing coefficients for interventions for the first variable and the second variable;

generating a second plurality of candidate sets of intervention tuples for the first variable and the second variable by repeatedly setting each mixing coefficient in the second system of equations to zero and solving the second system of equations using the set of intervention tuples for the first variable and the estimated probability distributions for the first variable and the second variable; and selecting a set of intervention tuples for the first variable and the second variable from the second plurality of candidate sets of intervention tuples.

13. A computer system comprising:

a processor; and a computer storage medium storing computer-useable instructions that, when used by the processor, causes the computer system to perform operations comprising:

receiving, by the processor, (i) a causal graph defining causal relationships among a plurality of variables, (ii) a set of baseline samples drawn from a baseline distribution associated with the causal graph, and (iii) a set of samples drawn from a mixture distribution corresponding to a mixture of interventions affecting at least a portion of the set of samples;

estimating, from the set of baseline samples and the set of samples drawn from the mixture distribution, one or more probability distributions over subsets of the plurality of variables;

enforcing positivity on the one or more probability distributions by perturbing at least one of the one or more probability distributions such that probabilities in the at least one of the one or more probability distributions are non-zero;

iteratively determining a final set of intervention tuples for the plurality of variables from the causal graph, each intervention tuple identifying (i) an intervention that sets one or more variables to respective values and (ii) a mixing coefficient representing a fraction of the set of samples drawn from the mixture distribution attributable to the intervention, the iteratively determining comprising:

selecting variables from the causal graph for a current iteration based on a topological ordering of the causal graph, determining a set of intervention tuples for N variables by forming a system of equations using the one or more probability distributions and enforcing exclusion by repeatedly setting a mixing coefficient to zero to generate a plurality of candidate sets of intervention tuples, lifting the set of intervention tuples for N variables to a set of intervention tuples for N+1 variables using (i) the set of intervention tuples for the N variables and (ii) estimated probability distributions for the N+1 variables, pruning intervention tuples having mixing coefficients below a threshold and renormalizing remaining mixing coefficients, and repeating the selecting, determining, lifting, and applying by incrementing N until the final set of intervention tuples is generated for the plurality of variables;

assigning each sample from at least a portion of the set of samples with interventions to an intervention using the final set of intervention tuples; and storing, in computer memory, an association between (i) sample identifiers for the portion of the set of samples and (ii) respective assigned interventions to provide a labeled dataset for a causal analytics process.

14. The system of claim 13, wherein determining the set of intervention tuples for a first variable at a first iteration comprises:

generating estimated probability distributions for the first variable by marginalizing data from the set of baseline samples and the set of samples with interventions, wherein generating the estimated probability distributions for the first variable includes perturbing the estimated probability distributions such that all probabilities are non-zero;

generating a first system of equations to determine mixing coefficients for interventions for the first variable;

generating a first plurality of candidate sets of intervention tuples for the first variable by repeatedly setting each mixing coefficient in the first system of equations to zero and solving the first system of equations using the estimated probability distributions for the first variable; and selecting the set of intervention tuples for the first variable from the first plurality of candidate sets of intervention tuples.

15. The system of claim 14, wherein a first mixing coefficient for a first intervention tuple in the set of intervention tuples the set of intervention tuples for the first variable is set to zero based on the first mixing coefficient being below a threshold and other mixing coefficients are renormalized based on setting the first mixing coefficient to zero.

16. The system of claim 14, wherein the set of intervention tuples for the first variable is selected from the first plurality of candidate sets of intervention tuples by:

computing an L2 norm for each candidate set of intervention tuples; and selecting a candidate set of intervention tuples with a lowest L2 norm.

17. The system of claim 14, wherein determining the set of intervention tuples for the first variable and a second variable at the first iteration comprises:

generating estimated probability distributions for the first variable and the second variable using the set of baseline samples and the set of samples with interventions;

generating a second system of equations to determine mixing coefficients for interventions for the first variable and the second variable;

generating a second plurality of candidate sets of intervention tuples for the first variable and the second variable by repeatedly setting each mixing coefficient in the second system of equations to zero and solving the second system of equations using the set of intervention tuples for the first variable and the estimated probability distributions for the first variable and the second variable; and selecting the set of intervention tuples for the first variable and the second variable from the second plurality of candidate sets of intervention tuples.

\* \* \* \* \*